(12) United States Patent
Yan et al.

(10) Patent No.: US 10,350,093 B2
(45) Date of Patent: Jul. 16, 2019

(54) DEGRADABLE IMPLANTABLE MEDICAL DEVICES

(71) Applicant: Elixir Medical Corporation, Sunnyvale, CA (US)

(72) Inventors: John Yan, Los Gatos, CA (US); Motasim Sirhan, Los Altos, CA (US); Brett Cryer, Sunnyvale, CA (US); Vinayak Bhat, Cupertino, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

(21) Appl. No.: 14/998,288

(22) Filed: Dec. 23, 2015

(65) Prior Publication Data

US 2016/0128849 A1 May 12, 2016

Related U.S. Application Data

(63) Continuation of application No. 11/398,363, filed on Apr. 4, 2006, now abandoned.
(Continued)

(51) Int. Cl.
*A61F 2/82* (2013.01)
*A61F 2/02* (2006.01)
(Continued)

(52) U.S. Cl.
CPC .................. *A61F 2/82* (2013.01); *A61F 2/02* (2013.01); *A61F 2/06* (2013.01); *A61F 2/07* (2013.01);
(Continued)

(58) Field of Classification Search
CPC ..... A61F 2/82–2002/91591; A61F 2210/0004; A61L 31/148; A61L 27/58
See application file for complete search history.

(56) References Cited

U.S. PATENT DOCUMENTS

| 4,273,137 A | 6/1981 | Pravoverov et al. |
| 4,645,503 A | 2/1987 | Lin et al. |

(Continued)

FOREIGN PATENT DOCUMENTS

| CN | 2304419 Y | 1/1999 |
| CN | 1250382 A | 4/2000 |

(Continued)

OTHER PUBLICATIONS

Chinese office action dated Dec. 11, 2009 for CN Application No. 200680018207.5.
(Continued)

*Primary Examiner* — Paul B Prebilic
(74) *Attorney, Agent, or Firm* — Wilson Sonsini Goodrich & Rosati

(57) ABSTRACT

Devices and methods are provided for an implantable medical device which is degradable over a clinically relevant period of time. The medical devices may have the form of implants, graft implants, vascular implants, non vascular implants, wound closure implants, sutures, drug delivery implants, biologic delivery implants, urinary tract implants, inter-uterine implants, organ implants, bone implants including bone plates, bone screws, dental implants, spinal disks, or the like. In preferred embodiments, the implantable medical device comprises an implantable luminal prosthesis, such as vascular and non-vascular stents and stents grafts.

48 Claims, 11 Drawing Sheets

Related U.S. Application Data

(60) Provisional application No. 60/668,707, filed on Apr. 5, 2005.

(51) Int. Cl.
| | | |
|---|---|---|
| *A61F 2/06* | (2013.01) | |
| *A61F 2/07* | (2013.01) | |
| *B23K 26/00* | (2014.01) | |
| *B23K 26/40* | (2014.01) | |
| *B23K 26/0622* | (2014.01) | |
| *B23K 26/382* | (2014.01) | |
| *B23K 26/352* | (2014.01) | |
| *A61F 2/90* | (2013.01) | |
| *B23K 101/06* | (2006.01) | |
| *B23K 103/02* | (2006.01) | |
| *B23K 103/12* | (2006.01) | |
| *B23K 103/00* | (2006.01) | |

(52) U.S. Cl.
CPC ...... *B23K 26/0006* (2013.01); *B23K 26/0624* (2015.10); *B23K 26/355* (2018.08); *B23K 26/382* (2015.10); *B23K 26/40* (2013.01); *A61F 2/90* (2013.01); *A61F 2210/0004* (2013.01); *A61F 2220/0058* (2013.01); *A61F 2250/003* (2013.01); *A61F 2250/0067* (2013.01); *B23K 2101/06* (2018.08); *B23K 2103/02* (2018.08); *B23K 2103/12* (2018.08); *B23K 2103/50* (2018.08)

(56) References Cited

U.S. PATENT DOCUMENTS

| | | | |
|---|---|---|---|
| 4,979,822 | A | 12/1990 | Sommer |
| 5,433,751 | A | 7/1995 | Christel et al. |
| 5,447,724 | A | 9/1995 | Helmus et al. |
| 5,496,359 | A | 3/1996 | Davidson |
| 5,522,895 | A | 6/1996 | Mikos |
| 5,649,977 | A | 7/1997 | Campbell |
| 5,674,286 | A | 10/1997 | D'Alessio et al. |
| 5,741,329 | A | 4/1998 | Agrawal et al. |
| 5,824,049 | A | 10/1998 | Ragheb et al. |
| 5,980,564 | A | 11/1999 | Stinson |
| 6,077,989 | A | 6/2000 | Kandel et al. |
| 6,174,329 | B1 | 1/2001 | Callol et al. |
| 6,235,061 | B1 | 5/2001 | Laurencin et al. |
| 6,240,616 | B1 | 6/2001 | Yan |
| 6,241,771 | B1 | 6/2001 | Gresser et al. |
| 6,287,332 | B1 | 9/2001 | Bolz et al. |
| 6,638,301 | B1 | 10/2003 | Chandrasekaran et al. |
| 6,840,961 | B2 | 1/2005 | Tofighi et al. |
| 6,854,172 | B2 | 2/2005 | Kaese et al. |
| 7,297,157 | B2 | 11/2007 | Chandrasekaran et al. |
| 7,402,173 | B2 | 7/2008 | Scheuermann et al. |
| 7,488,444 | B2 | 2/2009 | Furst et al. |
| 7,699,887 | B2 | 4/2010 | Burnside et al. |
| 7,879,109 | B2 | 2/2011 | Borden et al. |
| 7,879,367 | B2 | 2/2011 | Heublein et al. |
| 2001/0018610 | A1 | 8/2001 | Limon |
| 2002/0004060 | A1 | 1/2002 | Heublein et al. |
| 2002/0144757 | A1 | 10/2002 | Craig et al. |
| 2003/0033007 | A1 | 2/2003 | Sirhan et al. |
| 2003/0040790 | A1 | 2/2003 | Furst |
| 2003/0144728 | A1 | 7/2003 | Scheuermann et al. |
| 2003/0153971 | A1 | 8/2003 | Chandrasekaran |
| 2003/0199993 | A1 | 10/2003 | Gellman et al. |
| 2003/0204239 | A1 | 10/2003 | Carlyle et al. |
| 2003/0208256 | A1* | 11/2003 | DiMatteo ............ A61F 2/07 623/1.11 |
| 2003/0236320 | A1 | 12/2003 | Martin et al. |
| 2004/0098080 | A1 | 5/2004 | Lau et al. |
| 2004/0158309 | A1 | 8/2004 | Wachter et al. |
| 2005/0071016 | A1 | 3/2005 | Hausdorf et al. |
| 2006/0229711 | A1 | 10/2006 | Yan et al. |
| 2006/0241742 | A1 | 10/2006 | Harder et al. |
| 2009/0208555 | A1 | 8/2009 | Kuttler et al. |
| 2010/0131046 | A1 | 5/2010 | Santos et al. |
| 2011/0022158 | A1 | 1/2011 | Atanasoska et al. |
| 2011/0301694 | A1 | 12/2011 | Heublein et al. |
| 2011/0307053 | A1 | 12/2011 | Gale et al. |
| 2018/0318063 | A1* | 11/2018 | Kalb ............... A61F 2/06 |

FOREIGN PATENT DOCUMENTS

| | | | |
|---|---|---|---|
| CN | 2383533 | Y | 6/2000 |
| CN | 1262133 | A | 8/2000 |
| CN | 2542279 | Y | 4/2003 |
| CN | 1524590 | A | 9/2004 |
| CN | 1557507 | A | 12/2004 |
| CN | 1557511 | A | 12/2004 |
| DE | 19731021 | A1 | 1/1999 |
| DE | 19856983 | A1 | 12/1999 |
| DE | 102004043231 | A1 | 3/2006 |
| EP | 0966979 | A2 | 12/1999 |
| EP | 0221570 | B2 | 10/2000 |
| EP | 1389471 | A1 | 2/2004 |
| JP | 2006223860 | A | 8/2006 |
| WO | WO-02053202 | A1 | 7/2002 |
| WO | WO-02056790 | A2 | 7/2002 |
| WO | WO-03009777 | A2 | 2/2003 |
| WO | WO-03037223 | A1 | 5/2003 |
| WO | WO-03063733 | A1 | 8/2003 |
| WO | WO-2004004597 | A2 | 1/2004 |
| WO | WO2004010900 | A1 * | 2/2004 ............ A61F 2/91 |
| WO | WO-2004010900 | A1 | 2/2004 |
| WO | WO-2006108065 | A2 | 10/2006 |
| WO | WO-2006108065 | A3 | 6/2007 |

OTHER PUBLICATIONS

European search report dated Apr. 10, 2013 for EP Application No. 06740576.1.
International search report and written opinion dated Apr. 30, 2007 for PCT/US2006/012725.
Office action dated Mar. 21, 2014 for U.S. Appl. No. 11/398,363.
Office action dated Mar. 23, 2011 for U.S. Appl. No. 11/398,363.
Office action dated Apr. 20, 2010 for U.S. Appl. No. 11/398,363.
Office action dated Jun. 25, 2015 for U.S. Appl. No. 11/398,363.
Office action dated Oct. 14, 2014 for U.S. Appl. No. 11/398,363.
Stejskel, V. Metals as a common trigger of inflammation resulting in non-specific symptoms: diagnosis and treatment. Isr Med Assoc J. Dec. 2014;16(12):753-8.
EP16198729.2 Extended Search Report dated Sep. 1, 2017.
Co-pending U.S. Appl. No. 60/668,707, filed Apr. 5, 2005.
EP14177702.9 Notice of Opposition Ref. No. P31314EP-D1-PCT dated Aug. 21, 2017.
European office action dated Oct. 8, 2015 for EP Application No. 06740576.1.
European search report and search opinion dated Sep. 25, 2014 for EP Application No. 14177702-9.
Yao, et al. An XPS investigation of the oxidation/corrosion of melt-spun Mg. Applied Surface Science. vol. 158, Issues 1-2, May 1, 2000, pp. 112-119.

\* cited by examiner

DEGRADABLE IMPLANTABLE MEDICAL DEVICES

CROSS-REFERENCE TO RELATED APPLICATIONS

This application is a continuation of U.S. patent application Ser. No. 11/398,363, filed Apr. 4, 2006, which is presently abandoned and which claims priority to U.S. Provisional Patent Application No. 60/668,707, filed on Apr. 5, 2005, the entire content of which are incorporated herein by reference for all purposes.

BACKGROUND OF THE INVENTION

1. Field of the Invention

The present invention relates to medical devices and methods. More particularly, the present invention relates to implantable luminal prostheses and other medical devices which degrade in a body environment.

2. Description of the Background Art

Coronary artery disease is the leading cause of death in the industrialized countries around the world. It begins as the accumulation of atherosclerotic deposits in the walls of the major arteries which supply blood to the heart. As the deposits accumulate, normal blood flow to the heart is restricted. The heart has several compensatory mechanisms, which, to a point, can offset such diminished blood flow. Beyond these compensatory mechanisms, a number of well established pharmaceutical treatments have been shown to improve both symptoms and mortality in patients with mild to moderate coronary artery disease. However, as the disease progresses, its symptoms become more apparent, despite drug therapy. When the heart does not get enough blood, particularly during exercise or stress, advanced coronary artery disease is manifested as debilitating chest pain or angina. At this point, mechanical intervention is required to increase the amount of blood flowing to the heart.

Angioplasty is one of the most common interventional treatments for advanced coronary artery disease. Andreas Gruntzig performed the first percutaneous transluminal coronary angioplasty (PTCA) procedure. He advanced a catheter with a small balloon through the aorta and into a coronary artery with a partial occlusion. He then inflated the balloon, compressing the plaque against the arterial wall, and restoring blood flow to the heart.

PTCA has grown rapidly, and angioplasty catheters have become smaller and more maneuverable, allowing interventional cardiologists to access more difficult coronary blockages. However, restenosis, or reocclusion of the treated lesion, has plagued PTCA. Typically 30-40% of all patients have restenosis following PTCA.

Coronary stents were introduced in the mid 1990's to prevent restenosis. A stent is a small metal coil, slotted tube, mesh or scaffold structure that is placed in a coronary artery. It is a permanent implant that remains in the coronary artery following PTCA. The stent helps hold the artery open, improves the flow of blood, and relieves symptoms of coronary artery disease. Coronary stents were the first devices proven to reduce restenosis, dropping the rate of restenosis to 15-20%. Stents have since been used in the majority of PTCA procedures.

Conventional stents have taken two forms, balloon expandable stents and self-expanding stents. Both are typically made of metallic materials and may include a biocompatible coating. Such stents are permanently implanted into the human body by deploying them on or through a catheter. Such permanent implantation may increase the amount of intimal hyperplasia, thrombosis or other adverse medical effects. Coronary stents accomplish a lower restenosis rate of 15-20% post angioplasty compared to PTCA alone as a result of maintaining a higher acute gain post procedure.

Drug eluting stents, which elute drugs such as rapamycin and paclitaxel, were designed to further reduce intimal hyperplasia rates with stents. Such drug eluting stents incorporate metal or metal alloys with degradable or non degradable polymers which control release of the drug. The use of such drugs has further reduced the rates of restenosis as compared to stents alone.

The metals or metal alloys used for both conventional and drug eluting stents are intended to be biologically stable and remain in the body for the patient's life unless surgically removed at a later date along with surrounding tissue. Thus, these stents do not permit temporary placement within the body unless patient and surgeon are prepared to undertake a second procedure to remove the stent, which is difficult or impossible in most cases.

Although one of the primary functions of stenting is to provide mechanical support to the blood vessel wall and to preserve the lumen for blood flow, once the vessel wall heals the stent serves little or no continuing purpose. Further, the presence of a stent which remains mechanically rigid could potentially cause complications to the patient. It has therefore been desired to provide a stent which dissolves or degrades during or shortly after healing of the vessel or thereafter There have been several attempts to make stents from biodegradable polymer materials such as poly-lactic acids (PLA). Such polymer stents, however, tend to provide less mechanical support for the vessel wall and therefore have to be substantially thicker than a comparable metallic stent. The thickness can reduce the available blood flow lumen and can cause undesirable biologic responses.

Recent attempts have been made to make metal stents which decompose in the body, as described for example in U.S. Pat. No. 6,287,332 B1 and U.S. Pat. No. 6,854,172 B2. See also US2004/009808 and WO 02/053202. Such degradable metal stents, however, often compromise strength, profile, and other desirable characteristics which are found in conventional metal stents.

For these reasons, it would be desirable to provide degradable devices that have improved physical and mechanical characteristics. In particular, it would be desirable to provide a stent or other luminal prosthesis which is degradable during and/or upon healing of the vessel or thereafter and which has features to reduce the risk of injury to the vessel or restenosis. It would also be desirable to provide localized and controlled release of a pharmacological agent from the stent or other device for the treatment of blood vessels and other body structures at the location being treated with the stent. Such pharmacological agents could minimize both restenosis and any inflammatory response towards the stent or other device and degradation products thereof. At least some of these objectives will be met by the aspects of the present invention.

BRIEF SUMMARY OF THE INVENTION

Medical devices and methods utilize an implantable structure comprising a body which is degradable over a clinically relevant period of time. The body may have a variety of forms and may be used in a variety of medical treatments. In preferred embodiments, the body has the form of a stent, particularly a vascular stent of the type used in the treatment of coronary artery disease. The body comprises or is formed or constructed from a material which provides desired physical and mechanical attributes for the device. In preferred embodiments, the body comprises a metal (pure or with impurities), a metal alloy or a combination thereof. The term "metal" as used hereinafter will include such pure and impure metals as well as metal alloys and other combinations of two or more metals and metal alloys. The implantable bodies are at least partially degradable in a physiologic environment. Preferably, the materials of implantable structures are fully degradable so that no structure remains after a clinically relevant time period, as discussed below, and produce degradation byproducts which are physiologically benign, preferably being of a type which is naturally occurring in the body environment. More preferably, the bodies of the implantable structures produce degradation byproducts in amounts lower than what is typically present in the physiologic environment. The degradation rate of the implantable structure may be controlled in a variety of aspects individually or in combination thereof. Exemplary physiologic environments include vascular and other body lumens including the ureter and the urethra, solid tissues, cerebral tissue, and the like.

In a first aspect of the present invention, the degradation rate of the body of the implantable structure is controlled by selection of the composition of the implant material. The implant material is selected from a metal or metal alloys or combination thereof which can degrade in a clinically relevant time period ranging from approximately one month to 5 years, usually from 4 months to 2 years, and often from 6 months to one year. Thus, the weight or volume of the implantable structure will typically diminish each day by a percentage in the range from about 0.05% to 3%, usually from 0.1% to 0.75% per day, and more usually from 0.25% to 0.5% per day.

The metal, alloy, or combination material of the implantable structure will usually have a corrosion current (Icorr) in the range from 0.0001 amps/cm.sup.2 to 0.1 amps/cm.sup.2, usually from typically 0.001 amps/cm.sup.2 to 0.01 amps/cm.sup.2, and usually from 0.0025 amps/cm.sup.2 to 0.008 amps/cm.sup.2. The corrosion current is proportional to the corrosion rate, so materials with higher Icorr values will corrode more rapidly in the vascular or other physiologic environment. Icorr varies with the material property, geometry, and surface characteristics of the implant, and also physiologic environment among other factors. The Icorr value will typically represent an average value for the body as a whole or for any portion of the body.

In a second aspect, the degradation rate of the implantable structure is controlled at least in part by modifying its geometry. Such geometry modifications may include surface area to volume ratio. For example, attributes such as holes, reservoirs, trenches or others can be incorporated into the body to increase the surface area without significantly increasing the volume which can be used to control the degradation rate of the structure. When the implantable body comprises a stent having a strut, the geometry to be modified may include the strut width to strut thickness ratios.

In a third aspect of the present invention, the degradation rate of the implantable structure is controlled at least in part by the addition of corrosion inducing features. For example, in some embodiments, the implantable structure comprises an implantable body having at least one surface and at least one corrosion inducing feature on the at least one surface which causes at least a portion of the structure to degrade at a controlled degradation rate. In preferred embodiments, the implantable body comprises a metal, a metal alloy or a combination thereof. In some embodiments, the corrosion inducing feature comprises a pit, pore, partial hole, void or combination of these. In other embodiments, the corrosion inducing feature comprises a surface irregularity, scratch, streak, ridge, bump, texture, sintered porous metal or alloy, roughened surface or combination of these. In still other embodiments, the corrosion inducing feature comprises a hole, either partial or complete sintered pores, or combination of these. Further, in some embodiments, the implantable body has a first surface with a first associated portion of the body and a second surface with a second associated portion of the body, wherein the first surface has corrosion inducing features present in a density and/or configuration which causes the first associated portion to degrade at a rate which differs from the second associated portion.

Exemplary metals include iron, cobalt, tungsten, molybdenum, silver, and the like. These metals may be substantially pure, typically having purities about 90% by weight, often above 95% by weight, and frequently above 99.5% by weight. Alternatively, these metals may be combined as alloys with other metals or materials. Exemplary alloys include iron-containing alloys, such as AISI series 1000 carbon steels, AISI series 1300 manganese steels, AISI series 4000 molybdenum steels, AISI series 4100 chromium-molybdenum steels, AISI series 4300 and AISI series 8600 nickel-chromium-molybdenum steels, AISI series 4600 nickel-molybdenum steels, AISI series 5100 chromium steels, AISI series 6100 chromium-vanadium steels, AISI series 9200 silicon steels, and the like. Other iron-containing alloys will have at least 25% iron, preferably 50% iron, more preferably 75% iron, and often 90% iron, 95% iron, or 99% iron, or greater by weight. Iron alloys may contain carbon ranging from 0.05% to 3% by weight, preferably 0.05% to 1.0% by weight, more preferably 0.1% to 0.6% by weight. Alloys of silver, tin, cobalt, tungsten, molybdenum, and the like, will usually have at least 25% by weight of the pure metal, usually at least 50% by weight, often at least 75% by weight, and sometimes 90% by weight, 95% by weight, or 98% by weight, or greater.

In a fourth aspect of the present invention, the degradation rate of the implantable structure is controlled at least in part by the manipulation of corrosion enhancing and/or corrosion resisting elements in the implant structure. Thus, atoms or compounds which lower the resistance of a metal or metal alloy to corrosion can be added to or increased if already present in these materials. Likewise, one or more corrosion resisting elements may be depleted. Such manipulation of elements may occur on a surface of the implant structure, throughout the implant structure or adjacent to a grain boundary of a metal or alloy to control corrosion of the metal or alloy.

In a fifth aspect of the invention, the degradation rate of the implantable structure is controlled at least in part by the addition of corrosion controlling agents. Such agents may be synthetic or biologic, such as acidic compounds, sodium chloride, calcium chloride, magnesium chloride, hydrochloric acid, citric acid, amino acid, hydroxyapatite, hydrogen peroxide, basic compounds such as potassium hydroxide, acidic and basic pharmaceutical agents, or polymers with acidic or basic byproducts, others or a combination thereof.

In a sixth aspect of the invention, the degradation rate of the implantable structure is controlled at least in part by the creation of a galvanic cell. In some embodiments, metal or alloy particles are delivered adjacent to the implant structure, either in fluid or tissue. These particles are in fluid contact with the implant and create a corrosion-inducing galvanic cell. Galvanic cells can be created, for example, by alloying metals having different electrochemical potentials so that a current may be generated to oxidize the alloy in the electrolytic physiologic environment.

In a seventh aspect of the invention, the degradation rate of the implantable structure is controlled at least in part by layering of materials. In some embodiments, the implantable structure comprises an implantable body having a first layer which degrades at a first degradation rate and a second layer which degrades at a second degradation rate which differs from the first rate. The first layer and second layer comprises a metal, metal alloy or combination thereof and the layers cause at least a portion of the structure to degrade at a controlled degradation rate. The first and second layers may have different passive states. The first and second layers may differ in an electrochemical series. Alternatively or in addition, the degradation period and/or degradation rates may differ due to differing thicknesses of the layers.

In an eighth aspect of the invention, the degradation rate of the implantable structure is controlled at least in part by incorporating or manipulating a protective layer. In some embodiments, the implantable structure comprises an implantable body comprising a metal, metal alloy or combination thereof having a degradation rate, and a layer which covers at least a portion of the implantable body, wherein aspects of the layer are controlled which controls the degradation rate of the implantable body. The protective layer may comprise a passivation layer or a coating. Such coatings may comprise a polymer, metal, metal alloy, therapeutic agent, corrosive agent, radiopaque agent or combination of these. Such aspects of the protective layer may include thickness, chemical composition, chemical permeability, durability, amount of coverage of the implantable structure, or a combination of thereof, such aspects of the protective layer may include amount of corrosion-resistant oxides. Optionally, the protective layer may have openings which reveal underlying portions of the implantable body, wherein the openings assist in controlling the degradation rate of the implantable body.

In further aspects of the invention, an implantable structure is provided comprising an implantable body comprising a metal, metallic alloy or combination thereof which has at least a portion which degrades at a controlled degradation rate, wherein the controlled degradation rate has at least two phases of differing degradation rates. In some embodiments, the at least two phases comprises an initial degradation rate which is slower than a later degradation rate. In other embodiments, the at least two phases comprises an initial degradation rate which is faster than a later degradation rate.

In another aspect of the invention, an implantable structure is provided comprising an implantable body comprising a metal, metallic alloy or combination thereof which has at least a portion which degrades at a controlled degradation rate which varies along its structure. In preferred embodiments, the implantable body comprises a stent.

In yet another aspect of the invention, an implantable structure is provided comprising an implantable body comprising a metal, metal alloy or combination thereof having a controlled degradation rate, and at least one therapeutic agent which elutes from the implantable structure. In some embodiments, the therapeutic agent includes a pharmacological agent including but not limited to an anti-cancer agent, an anti-inflammatory agent, an immuno suppressive agent, antiproliferative, antiplatelet, or a combination of these. In another aspect, the implantable structure further comprises at least one coating which at least partially covers the implantable body. The therapeutic agent may be contained in or adjacent to the coating. The coating may be metallic, polymeric, ceramic; synthetic or natural; and or combination thereof. The coatings may be degradable, partially degradable, non degradable, and or combination thereof. In other embodiments, the therapeutic agent comprises one therapeutic agent which elutes in one phase of degradation and another therapeutic agent which elutes in another phase of degradation. Further, in other embodiments, the therapeutic agent is at least partially contained in a corrosion inducing feature.

Other objects and advantages of the present invention will become apparent from the detailed description to follow, together with the accompanying drawings.

DETAILED DESCRIPTION OF THE INVENTION

The devices of the present invention may have a variety of forms and may be used in a variety of medical treatments. In preferred embodiments, the device has the form of a vascular stent that is used in the treatment of vascular disease. It may be appreciated that stents may be used in a variety of body lumens, such as an artery, vein, biliary duct, or esophagus.

In other embodiments, the devices of the present invention have the form of a variety of implants, such as graft implants, vascular implants, non-vascular implants, implantable luminal prostheses, wound closure implants, drug delivery implants, sutures, biologic delivery implants, urinary tract implants, inter-uterine implants, organ implants, bone implants including bone plates, bone screws, dental implants, spinal disks, or the like. The devices typically allow for one or more of the following: support, contain, hold together, affix, plug, close, deliver drug, deliver biologics to an organ, vessel, conduit, or bone for the treatment of hyper-proliferative diseases, restenosis, cardiovascular disease, wound healing, cancer, aneurysm, diabetic disease, abdominal aortic aneurysm, hyper-calcemia, ischemia, fibrillation, arrhythmia, or others.

Thus, the following detailed description utilizes the stent as a means of illustrating the invention by way of example and is not intended to limit the scope of the invention.

Implant as a Stent

Figure 1:
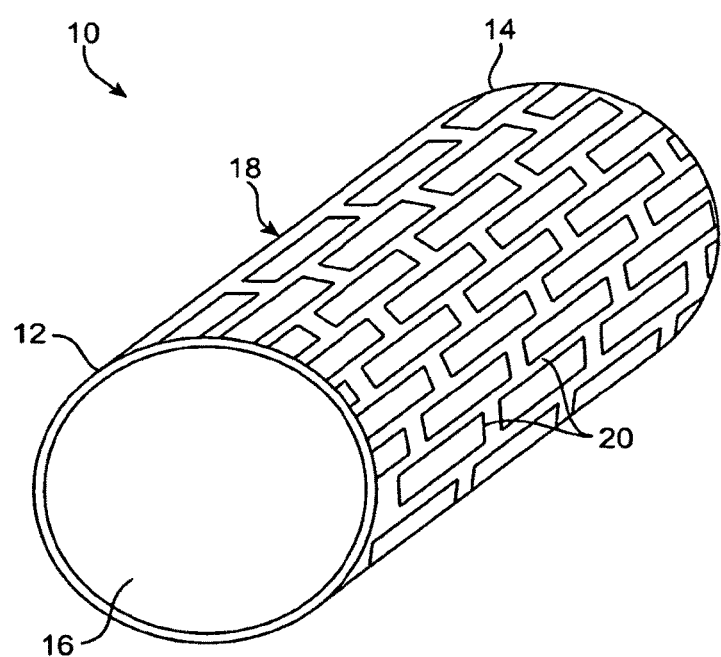
FIG. 1 illustrates an example of an embodiment of the implant of the present invention in the form of a stent.

In preferred embodiments, the implant has the form of a stent. Stent designs include coils, slotted tubes, corrugated rings, sheets, rolled sheets, locking designs, and stent grafts, to name a few. FIG. 1 illustrates an embodiment of a stent 10 in an expanded state. As shown, the stent 10 has a first end 12, a second end 14 and a central lumen 16. A stent body 18 extends from the first end 12 to the second end 14. The body 18 has struts 20 which form a lattice-type structure. The struts 20 may have circular, rectangular or other shape cross-sections. Typically, strut thicknesses range from approximately 0.0005" to 0.010", preferably approximately 0.001" to 0.004", more preferably approximately 0.0015" to 0.003". Strut widths typically range from approximately 0.001" to 0.008", preferably approximately 0.002" to 0.004".

The stents 10 may be self-expanding or balloon expandable. Stent pre-expansion diameters typically range from approximately 0.3 mm to 10 mm, preferably approximately 0.5 mm to 4 mm, more preferably approximately 0.8 mm to 2 mm. Stent post expansion diameters typically range from approximately 1.5 mm to 35 mm, preferably approximately 2 mm to 10 mm, more preferably approximately 2 mm to 5 mm. Depending on the material(s) from which the stent 10 is formed, the material(s) typically have a percent elongation range from approximately 5% to 100%, preferably approximately 15% to 70%, more preferably approximately 20% to 50%.

Degradation of Implant

As stated previously, the devices of the present invention are degradable in a biological environment. It may be appreciated that the terms degradation, biodegradation, dissolution, bioabsorption, absorption, resorption, corrosion, erosion, bioerosion, erodible, bioerodible and disintegration are used interchangeably along with other terms which describe any such deterioration in mass, volume or function by chemical, biological, electrical, mechanical, or any other means, unless stated otherwise.

It may also be appreciated that degradation as related to the present invention is considered to be degradation within a clinically relevant time period, such as approximately one month to 5 years. Although common metals or alloys may corrode at much longer rates ranging up to 1000 years or more depending on the inherent properties of the materials and the environmental conditions, such metals or metal alloys are considered nondegradable in a clinical setting. In preferred embodiments, the devices of the present invention substantially degrades in the body environment in the range of approximately one month to 5 years, preferably approximately 4 months to 2 years, more preferably approximately 6 months to 1 year. In some embodiments, the devices at least partially degrade in the body environment in less than one month, such as a few weeks, one week, a few days, one day, a few hours, one hour or less. For example, the device may have at least a portion which degrades at a controlled degradation rate to approximate dissolution at or within one month. Body environments effecting degradation typically have local tissue pH ranges from approximately 3 to 10, usually approximately 5 to 9, typically approximately 6 to 8.

Degradation of devices of the present invention may occur in multiple phases, such as a slower degradation rate in one phase and a faster degradation rate in another phase. In some embodiments, the device degrades at a slower rate in an initial phase and a faster rate in a later phase. In other embodiments, the devices degrade at a faster rate in an initial phase and slower rate in a later phase. Likewise, degradation may be uniform along the structure or variable along the structure. The average mass or volume percentage loss may range from approximately 3% per day to 0.05% per day, preferably approximately 0.75% per day to 0.1% per day, more preferably approximately 0.5% per day to 0.25% per day.

When the implant is comprised of a metal or metal alloy, degradation of the implant produces byproducts such as metal ions, salts or complexes. Preferably, these byproducts are naturally occurring elements in the body environment or cause no significant harmful effects. More preferably, the implantable structures produce degradation byproducts in amounts lower than what is typically present in the body environment. Further, the rate of degradation of the implant may be controlled to minimize the possibility of any negative biologic response from the degradation byproducts. Currently, long-term anti-platelet therapy is recommended for patients undergoing permanent implantation of conventional non-degradable devices, such as stents, to prevent acute thrombosis or late thrombosis. Systemic anti-platelet therapy has side effects such as internal bleedings. Long-term anti-platelet therapy may not be necessary when degradable implants of the present invention are used since the risk of thrombosis is reduced once the implant has dissolved. This may lower procedure-associated cost and also minimize risks associated with patient compliance of daily doses of drugs. As an example, when the implant comprises or consists essentially of iron or an iron alloy, the degradation products may include biocompatible iron species such as oxidized iron species of a type which naturally occur in the human body. By controlling the degradation rate, the concentration of these species can be kept below 10 fold the normal amounts, preferably below five fold, more preferably below two fold, and most preferably at a level no greater than naturally present in the body. A particular preferred metal is a carbon steel where the degraded species will include primarily or exclusively iron and carbon compounds.

Metals and Metal Alloys

In preferred embodiments, the devices of the present invention comprise at least partially degradable metals, metal alloys, or a combination thereof.

Examples of metals include Cobalt, Tungsten, Bismuth, Silver, Copper, Iron, Zinc, Magnesium, Zirconium, Molybdenum, Indium, Tin or other metals. In some embodiments, implant metal purity ranges from approximately 90% to 100%, preferably approximately 95% to 99.99%, more preferably from approximately 9.9.5 to 99.9% by weight.

Examples of metal alloys include: 1) silver containing alloys (such as silver-tin alloys, 2) cobalt containing alloys (such as cobalt-iron alloys), 3) iron containing alloys (such as 80-55-06 grade cast ductile iron, other cast ductile irons, AISI 1010 steel, AISI 1015 steel, AISI 1430 steel, AISI 8620 steel, AISI 5140 steel, or other steels, or others), 4) tungsten containing alloys, 5) melt fusible alloys (such as 40% bismuth-60% tin, 58% bismuth-42% tin, bismuth-tin-indium alloys or others), 6) magnesium alloys, 7) zinc alloys, 8) shape memory or superelastic alloys, and 9) other alloys, to name a few.

In some embodiments, the devices of the present invention are comprised of more than one metal or metal alloy. Examples of metal+metal implants include cobalt+tungsten, tungsten+iron, magnesium+iron, silver+zinc or others. Examples of metal+alloy implants include tungsten+8620 steel, titanium+low carbon steel, magnesium+1015 steel alloy, silver+bismuth-tin alloy or others. Examples of alloy+alloy implants include 8620 steel+silver-tin, 1015 steel+bismuth-tin or others.

Figure 2A:
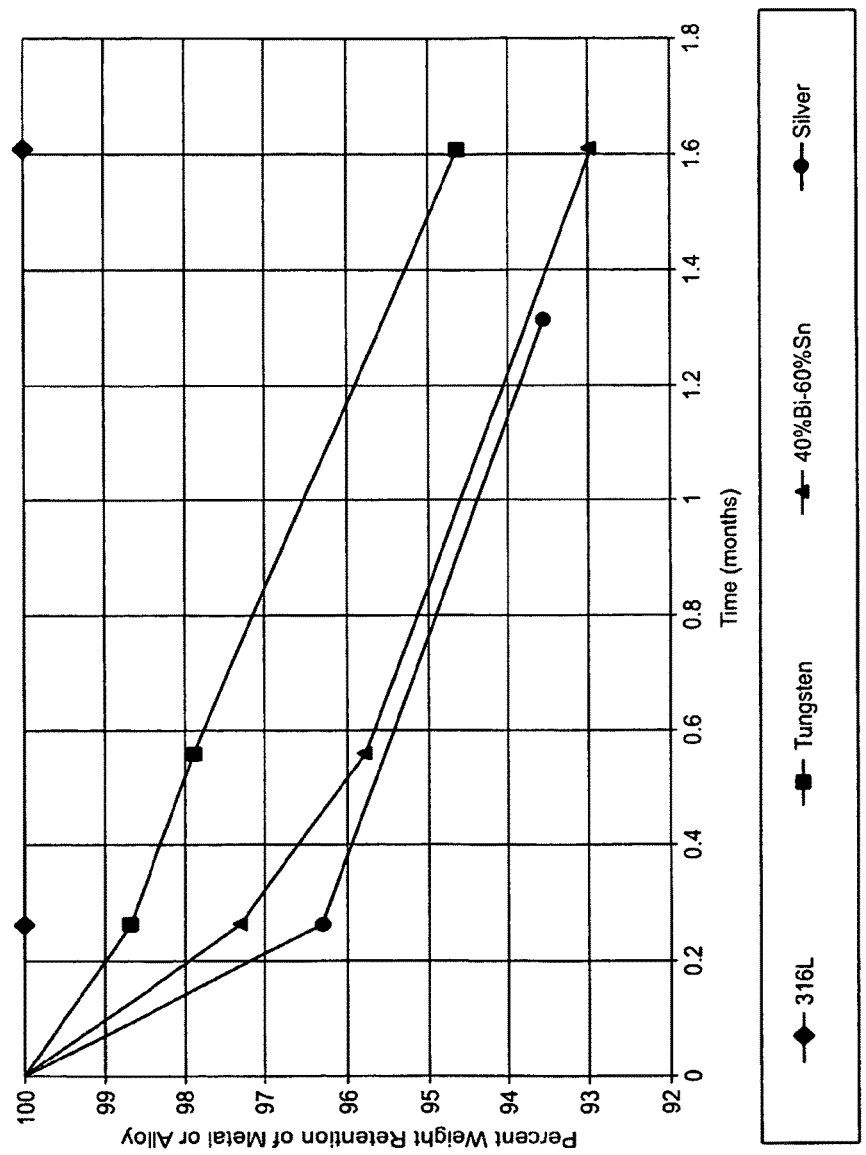
FIG. 2A shows examples of metal and metal alloy degradation data.
Figure 2B:
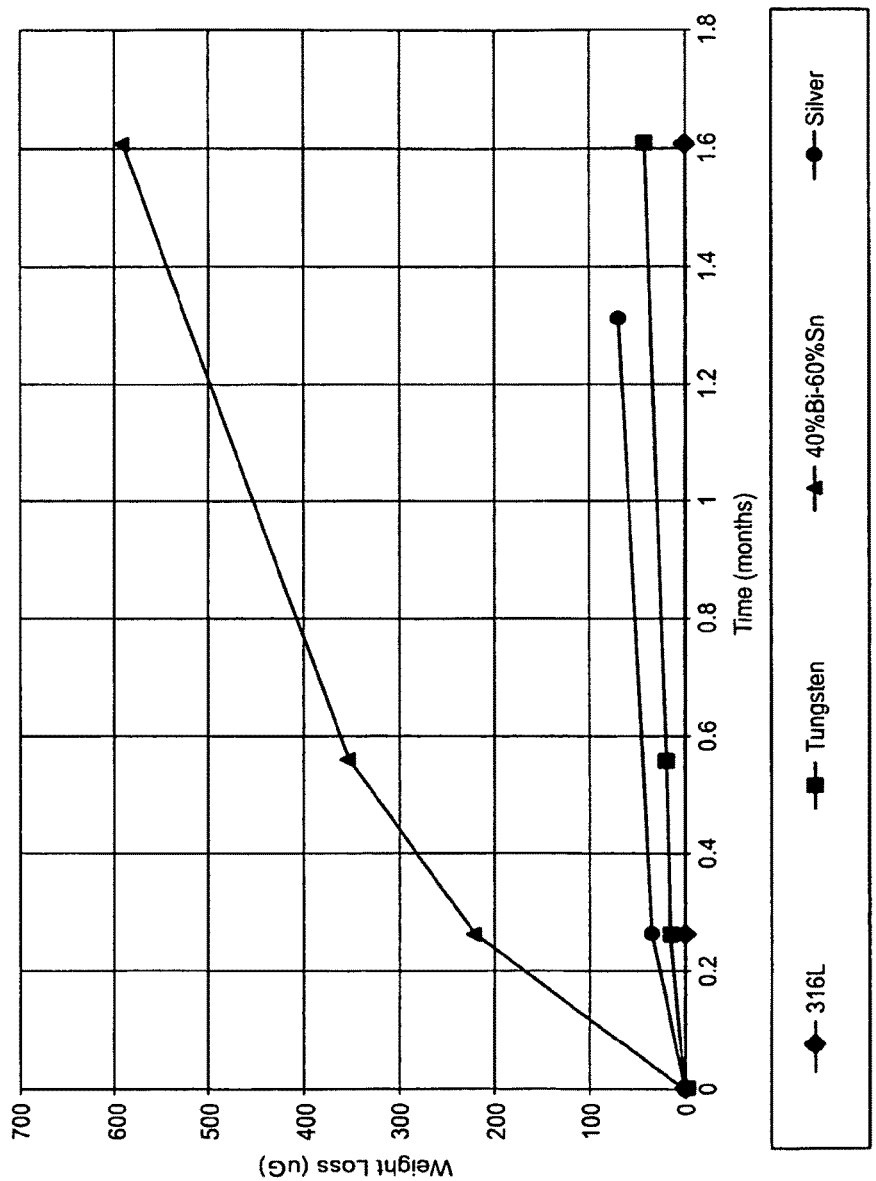
FIG. 2B illustrates data for weight loss over time of some metal and metal alloy implant materials as compared to stainless steel.

Examples of metal and metal alloy degradation data are illustrated in FIG. 2A. FIG. 2B illustrates weight loss data over time for some metal and metal alloy implant materials as compared to stainless steel.

Degradation of metals is commonly termed corrosion, and the terms "degradation" and "corrosion" are used interchangeably herein for all materials. Most metal corrosion occurs via electrochemical reactions at the interface between the metal and an electrolyte solution, such as found in the body environment. Corrosion typically occurs as a result of anodic and cathodic reactions.

The potential of the metal is the means by which the anodic and cathodic reactions are kept in balance. The equilibrium potential assumed by the metal in the absence of electrical connections to the metal is called the Open Circuit Potential, Eoc. The value of either the anodic or cathodic current at Eoc is called the Corrosion Current, Icorr. Icorr and Corrosion Rate are a function of many system variables including type of metal, solution composition, temperature, solution movement, metal history, and many others.

For implant in saline solution at 37.degree. C. temperature, the corrosion current flux (Icorr) is proportional to corrosion rate (CR) according to the following formula: CR=(Icorr×K×EW)/d CR The corrosion rate (mm/yr) Icorr The corrosion current (amps/cm$^2$) K Faraday's constant=3272 (mm/(amp-cm-year)) EW The equivalent weight (grams/equivalent) d Density (grams/cm$^3$)

Typical implants of the present invention degrading in physiological conditions will have Icorr (corrosion current) ranges from approximately 0.0001 amps/cm$^2$ to 0.1 amps/cm$^2$; preferably approximately 0.001 amps/cm$^2$, to 0.01 amps/cm$^2$, more preferably approximately 0.0025 amps/cm$^2$ to 0.008 amps/cm$^2$.

In some embodiments, after one month of degradation, the metal or metal alloy maintains greater than approximately 25% of strength, preferably greater than approximately 50%, more preferably greater than approximately 60% of strength as compared to strength prior to implantation. In these or other embodiments, after two months of degradation, the metal or metal alloy implant maintains greater than approximately 25% of strength, preferably greater than approximately 50%, more preferably greater than approximately 60% of strength as compared to strength prior to implantation. In these or other embodiments, after four months of degradation, the metal or metal alloy implant maintains greater than approximately 25% of strength, preferably greater than approximately 50%, more preferably greater than approximately 60% of strength as compared to strength prior to implantation.

In some embodiments, the implant will be corroded prior to implantation with an amount of corrosion greater than 0.01% by weight, preferably with greater than 0.1% by weight, and more preferably with greater than 1% by weight (based on the weight of the body prior to corrosion). In some embodiments, the corrosion prior to implantation may cover greater than 1% of the surface area, preferably greater than 5% of the surface area, and more preferably greater than 10% of the surface area of the body which will be exposed to the physiologic environment. In such cases, the corrosion may result from pretreatment or may be the result of the device being packaged in a sterile environment with an oxidizing atmosphere, e.g., oxygen and some moisture.

In some embodiments, the implant may corrode prior to implantation by less than 5% by mass, preferably less than 1% by mass, and more preferably less than 0.01% by mass. In some embodiments, the implant may corrode prior to implantation by less than 10% of the surface area, preferably less than 1% of the surface area, and more preferably less than 0.1% of the surface area.

Controlling Degradation Rates

Modifying Geometries

In some embodiments, the degradation rate of the implant is increased by maximizing the surface area to volume ratio. For example, when the implant is in the form of a stent, the stent strut thickness to width or width to thickness ratios may be greater than 1.4:1, preferably greater than 2:1, more preferably greater than 3:1. In preferred embodiments, the stent strut thickness is less than approximately 100 microns, preferably less than approximately 70 microns, more preferably less than approximately 50 microns. This minimizes absolute depth of degradation needed and minimizes localization of corrosion byproducts. Typically, the implant surface area/length ranges from approximately 0.001 cm$^2$/mm to 0.75 cm$^2$/mm, preferably approximately 0.005 cm$^2$/mm to 0.25 cm$^2$/mm, most preferably approximately 0.01 to 0.1 cm$^2$/mm.

In other embodiments, attributes such as holes, reservoirs, trenches or other can be incorporated in the implant to increase the surface area without significantly increasing the volume.

Addition of Corrosion Inducing Features

In some embodiments, corrosion inducing features are included in the body of the implant of the present invention to induce or assist degradation. Examples of corrosion inducing features present on at least one exposed surface include pits, pores, partial holes, voids, surface irregularities, scratches, streaks, ridges, bumps, texture, sintered porous metal or alloy, scoring, roughened surface, holes, thru holes, thru sintered pores, or other geometric or random features or combination thereof. Corrosion inducing features may be present on any surface of an implant, including surfaces of various shapes or design configurations, including examples where the implant has large holes, reservoirs, trenches or others. Such surface features will typically increase the degradation rate by 10% or more based on weight, often 20% or more based on weight, and frequently by 40% or more based on weight. Some surface features will be selected to provide a mean surface roughness (RA) greater than 100 nm, often greater than 400 nm, and frequently 1000 nm (1 µm) or greater. The surface features may be provided on the entire exposed surface area of the implant, or in other cases may be provided only on a portion of the exposed surface where it is desired to increase the degradation rate. It would be appreciated that non-uniform distribution of the surface feature(s) will often result in a non-uniform degradation profile on the implant.

In some embodiments, the rate of weight loss of the implant with corrosion inducing features is at least 10% greater, preferably, 20%, more preferably 40% greater than the same implant without features. Further, in some embodiments, the rate of dimension reduction of the implant with features is at least 10%, preferably 20%, more preferably 40% greater than the same implant without features.

Figure 3:
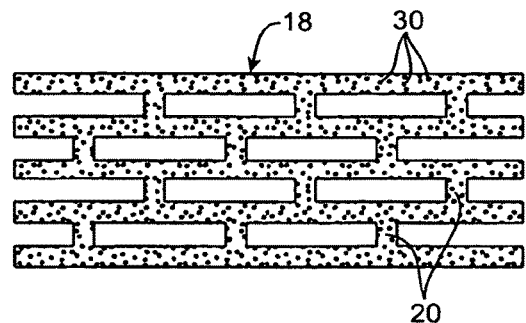
FIG. 3 illustrates a portion of a stent body having an example of corrosion inducing features thereon.
Figure 4:
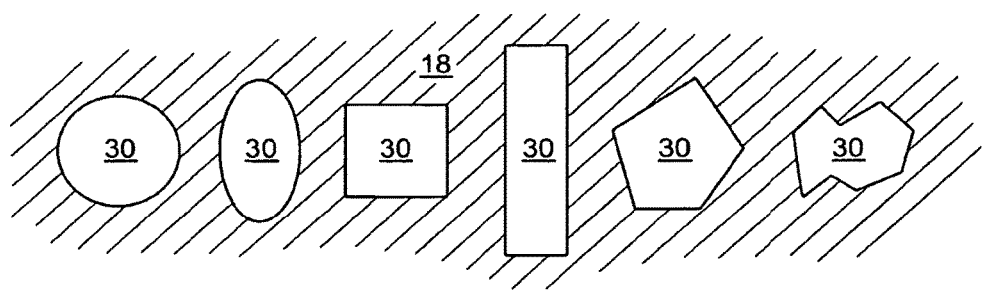
FIG. 4 provides a close-up illustration of examples of corrosion inducing features on a stent body.

FIG. 3 illustrates a portion of a stent body 18 (such as of the stent body 18 of FIG. 1) having examples of corrosion inducing features 30 thereon. FIG. 4 provides a close-up illustration of a variety of corrosion inducing features 30 on a stent body 18. As shown, the features 30 may have a variety of shapes, including circular, oval, square, rectangular, pentagonal, and polygonal, to name a few.

Figure 5:
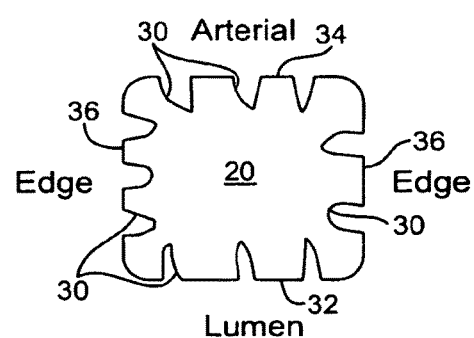
FIG. 5 illustrates a cross-section of a strut of a stent body having examples of corrosion inducing features extending therein.
Figure 6:
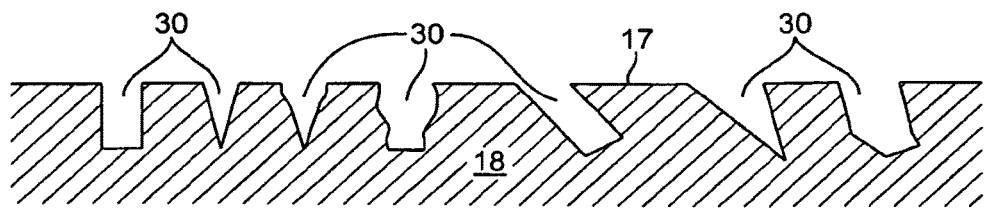
FIG. 6 illustrates a surface of an implant having examples of corrosion inducing features of a variety of shapes and sizes extending from the surface into the implant.
Figure 7:
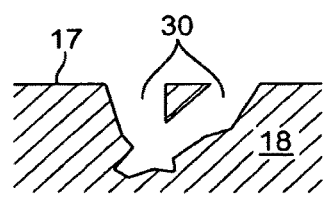
FIG. 7 illustrates cross section of an implant body with an example of corrosion inducing features which extend from the surface and cross or join within the implant.
Figure 8:
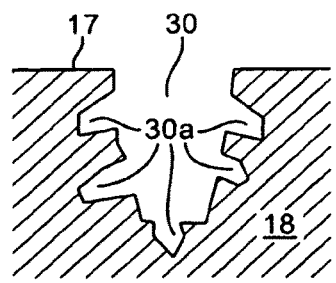
FIG. 8 illustrates an example of a corrosion inducing feature which extends from the surface and includes side-branches within the implant.
Figure 9:
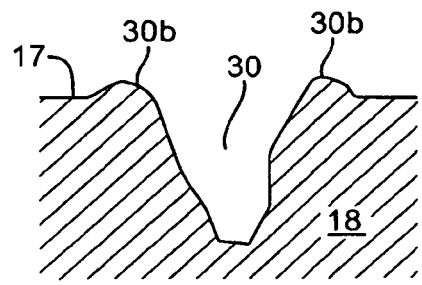
FIG. 9 illustrates an example of a corrosion inducing feature which extends from the surface into the implant and includes at least one protrusion which extends outwardly from the surface.

FIG. 5 illustrates a cross-section of a strut 20 of the stent body 18 of FIG. 3. In this embodiment, the strut 20 has a square cross-section. The strut 20 includes a lumen edge 32 which faces the lumen 16 of the stent 10, and an external edge 34 which faces the wall of the body lumen, such as an arterial wall. The strut 20 further includes side edges 36 which face other portions of the stent body 18 (i.e. other struts). Here, the strut 20 has corrosion inducing features 30 on each of the lumen edge 32, external edge 34 and side edges 36. These corrosion inducing features 30 include pits, pores, partial holes, voids, surface irregularities or others. FIG. 6 illustrates a surface 17 of a stent body 18 having corrosion inducing features 30 of a variety of shapes and sizes which extend from the surface 17 and into the stent body 18. FIG. 7 illustrates corrosion inducing features 30 which extend from the surface 17 and cross or join in the stent body 18. FIG. 8 illustrates a corrosion inducing feature 30 which extends from the surface 17 and includes side-branches 30a within the stent body 18. FIG. 9 illustrates a corrosion inducing feature 30 which extends from the surface 17 into the stent body 18 and includes at least one protrusion 30b which extends outwardly from the surface 17 of the stent body 18.

Figure 10:
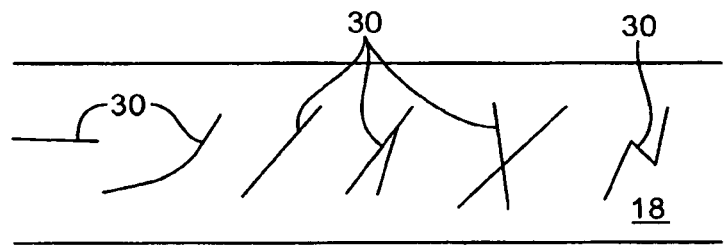
FIG. 10 illustrates examples of corrosion inducing features in the form of scratches.

FIG. 10 provides a top view illustration of a surface of a stent body 18 having corrosion inducing features 30 in the form of scratches. The scratches or streaks may have any length, depth, width, orientation or shape. Example shapes include straight lines, curved lines, diagonal lines, overlapping lines, crossed lines, zig-zag lines, to name a few.

Figure 11:
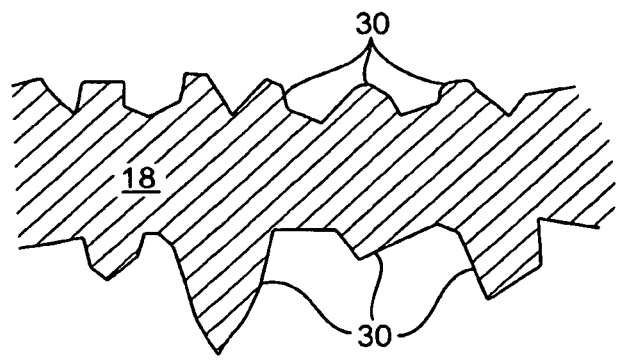
FIG. 11 illustrates a surface of an implant having examples of corrosion inducing features in the form of, textured surfaces.

FIG. 11 illustrates a surface of a stent body 18 having corrosion inducing features 30 in the form of textured surfaces. The resulting surface finish can be described by average roughness (Ra). The average roughness is the area between the roughness profile and its mean line, or the integral of the absolute value of the roughness profile height over the evaluation length. Surfaces of the implants of the present invention having such corrosion inducing features may have an Ra above approximately 100 nanometer, preferably an Ra above approximately 400 nanometer, and more preferably an Ra above approximately 1000 nanometer.

Figure 12:
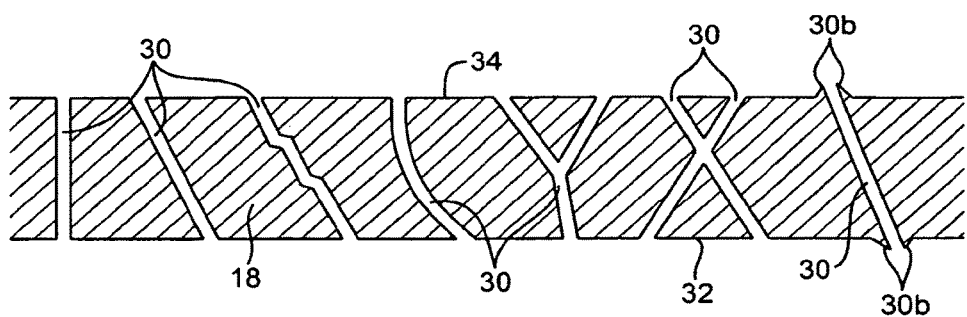
FIG. 12 illustrates a cross-section of a portion of an implant having examples of corrosion inducing features in the form of holes extending through the implant.
Figure 13:
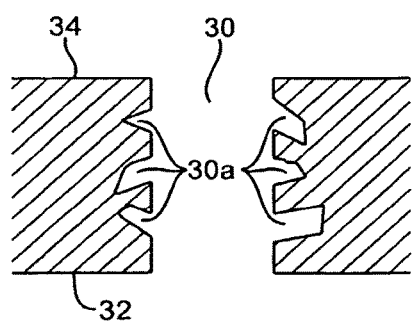
FIG. 13 illustrates an example of a hole including a plurality of side-branches.

FIG. 12 illustrates a cross-section of a portion of a stent body 18 having an external surface 34 and a lumen surface 32. Corrosion inducing features 30 in the form of holes are shown extending through the body 18 from the external surface 34 to the lumen surface 32. The holes may be smooth, jagged, straight, diagonal, curved, connected, or intersecting, to name a few. Further, in some embodiments, at least one protrusion 30b may extend outwardly from the surfaces 32, 34 of the stent body 18. FIG. 13 illustrates a corrosion inducing feature 30 in the form of a hole extending from an external surface 34 to a lumen surface 32 of a stent body 18, wherein the hole includes a plurality of side-branches 30a.

Creating Corrosion Inducing Features

Some of the above described corrosion inducing features can be formed by exposing the implant metal or alloy or combination thereof to chemicals, such as but not limited to hydrochloric acid, hydrofluoric acid, nitric acid, phosphoric acid, acetic acid, citric acid, formic acid, lactic acid, oxalic acid, aqua regia, fuming sulfuric acid others at various conditions or combination thereof.

Corrosion inducing features can also be formed by exposing the implant metal or alloy or combination thereof to salt spray, strong alkaline solutions such as sodium hydroxide, potassium hydroxide, solutions containing salts such as sodium, potassium carbonates, and phosphates, or other bases at various conditions. Or, the features can be formed by exposure of the implant to saline, sodium chloride, ferric chloride or other salt solution, Ferrolyte (Starlight Chemicals, Inc., Chicago, Ill.), or others at various conditions. Other chemicals which create such features include $AlCl_3$, $CaCl_3$ with $MgCl_2$, $CuSO_4$, $HgCl_2$, $H_2SiF_6$, $K_2CO_3$, $Na_2CO_3$, $Na_2HSO_3$, $NaOCl$, $Na_3PO_4$, $NH_4C_1$, $NH_2SO_3H$, $NI(NO_3)_2$, $ZnCl_4$, bromine, $H_2O_2$, gas oxidizer like oxygen, nitrogen, chlorine or other various conditions or combination thereof.

In another embodiment, corrosion inducing features are formed by exposure of the implant material to liquid metals at various conditions. Such liquid metals include bismuth, gallium, lithium, sodium, potassium, and sodium-potassium alloys, thorium-magnesium, zinc or others or combination thereof.

In another embodiment, corrosion inducing features are formed by methods such as but not limited to electron-induced etching, glow discharge plasma etching, laser-assisted etching, chemically assisted ion beam etching, laser-induced photochemical dry etching, pulsed plasma discharges, sputter beam, exposure to radioactive rays, positive ion beams, repetitive potentiodynamic polarization, ion bombardment, or other methods or combination thereof.

In another embodiment, corrosion inducing features are formed by placing the implant material in an electrolyte with a more noble metal for a sufficient period of time to form the desired corrosion inducing features.

Some corrosion inducing features, such as scratches or streaks, can be made with the use of a tool, such as a razor blade, needle, tweezers, sharp point indenter, engraver, knife, scalpel, bristle brush, steel wool, knurling tool, file, carbide burr, pointed pick, grind stone, tube cutter, chisel, scraper, laser, electro discharge machining (EDM), or other tools or combination thereof.

To obtain corrosion inducing features such as ridges, bumps, texture, or roughened surface a variety of methods can be used. Example methods include sandblasting, bead blasting, chemical etching, lasing, plasma etching, ion beam bombardment, electro discharge machining (EDM) imprinting, molding, sintering, chemical vapor deposition (CVD), sputtering, electroplating or other methods or combination thereof.

Some corrosion inducing features such as sintered pores, holes, and thru holes can be made by lasing, electro discharge machining, chemical etching with chemicals used for preparation of pits, partial holes, and voids, exposure to radioactive rays or ion beam, metal injection molding, sintering metal or alloy beads or other geometries, or other methods or combination thereof.

The corrosion inducing features can be formed during the manufacturing process or at any time prior to implantation. The features could also be formed in situ using a tool or a device such as rotablader, cutting balloon or other techniques or other mechanical, electrical, chemical means or a combination thereof.

Dimensions and Distribution of Corrosion Inducing Features

The corrosion inducing features may have any suitable size, diameter, width, length, depth, circumference or dimension, etc. In some embodiments, the mean diameter, width or length of the features on the implant surface range from approximately 1 nm to 1 mm, preferably approximately 10 nm to 100 micrometer, more preferably approximately 100 nm to 1 micrometer. The length of linear features such as streaks and scratches may be longer. In some embodiments, the mean depth of the features on the implant surface range from approximately 1 nm to 10 mm, preferably approximately 10 nm to 1 mm, more preferably approximately 100 nm to 1 micrometer. The features can be of similar dimensions or can vary in size or shape. Features can be contained or partially contained in other features.

Figure 14:
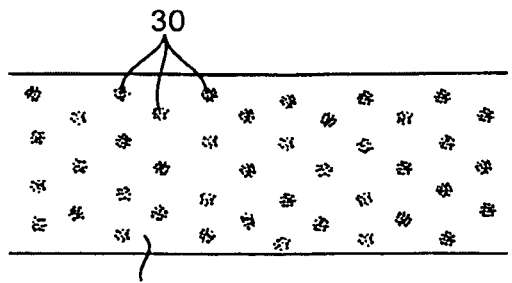
FIG. 14 illustrates an example of corrosion inducing features substantially uniformly distributed across a surface of an implant.
Figure 15:
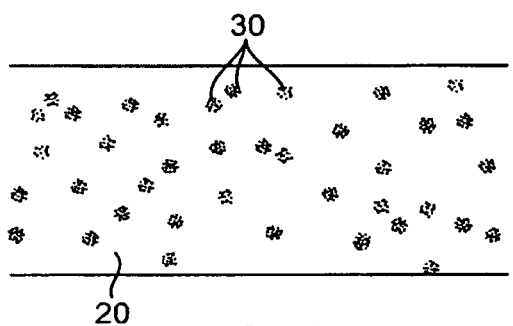
FIG. 15 illustrates an example of corrosion inducing features of FIG. 14 non-uniformly distributed across a surface of an implant.
Figure 16:
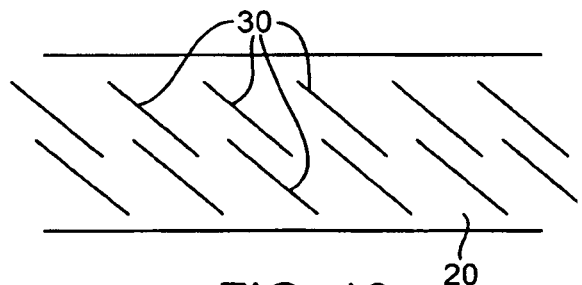
FIG. 16 illustrates an example of corrosion inducing features in the form of streaks substantially uniformly distributed across a surface of an implant.
Figure 17:
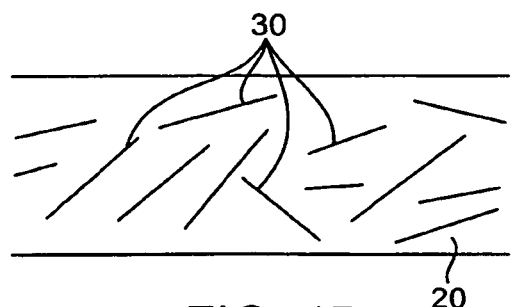
FIG. 17 illustrates an example of corrosion inducing features of FIG. 16 non-uniformly distributed across a surface of an implant.

The corrosion inducing features can be uniformly or non-uniformly distributed on the implant surface. FIG. 14 illustrates corrosion inducing features 30 substantially uniformly distributed across a surface of an implant, such as a stent strut 20. Here, the features 30 include pits, pores, holes, voids or surface irregularities. FIG. 15 illustrates these corrosion inducing features 30 non-uniformly distributed across a surface of an implant, such as a stent strut 20. Similarly, FIG. 16 illustrates corrosion inducing features 30 substantially uniformly distributed across a surface of an implant, such as a stent strut 20. Here, the features 30 include streaks. FIG. 17 illustrates these corrosion inducing features 30 non-uniformly distributed across a surface of an implant, such as a stent strut 20.

The corrosion inducing features can be partially or fully covering the implant surface. The features can be on one or more surfaces of the implant, such as the external surface, the lumen surface, edges or other surfaces. The features can be limited to one or more areas where it is desirable to for the implant to degrade while other areas remain intact or not degrade. The features can be present in variable densities at different locations on the surface of the implant. One or more areas can degrade faster than other areas. Thus, the degradation rate of the implant can be controlled in longitudinal, circumferential or other directions. As an example, the proximal and distal ends of an intraluminal stent can degrade before a section therebetween.

The surface density of the corrosion inducing features, such as pits, pores, partial holes, thru holes, voids, or surface irregularities, on the implant surface can range from approximately $1/cm^2$ to $1 \times 10^{14}/cm^2$, preferably approximately $100/cm^2$ to $1 \times 10^8/cm^2$, more preferably approximately $1000/cm^2$ to $1 \times 10^6/cm^2$. The percentage of the implant surface without features can range from approximately 0% to 99.9%, preferably approximately 5% to 75%, more preferably approximately 10% to 50%.

Manipulation of Corrosion Enhancing/Resisting Elements

Alternatively or in addition to corrosion inducing features, implants of the present invention may be comprised of a material, such as metal or metal alloy, which has enrichment of one or more corrosion enhancing elements. Thus, atoms or compounds which lower the resistance of the metal or metal alloy or combination thereof, to corrosion can be added to or increased if already present in these materials. For example, an alloy may be processed to enrich elements like carbon, iron, copper, silicon, calcium, sulphur, magnesium sulphide, silicates or other elements within the alloy, or deplete certain elements like chromium, nickel, molybdenum or other corrosion resistant elements. In some embodiments, corrosion enhancing elements can be added to have a composition of greater than approximately 0.1%, preferably greater than approximately 1% more preferably greater than approximately 5%. Likewise, one or more corrosion resisting elements may be depleted.

Such manipulation of elements may occur on a surface of the implant, throughout the implant or adjacent to a grain boundary of the alloy to control corrosion of the alloy. In some embodiments, metals or metal alloys have corrosion inducing elements greater than approximately 0.01% composition by weight, preferably greater than approximately 1%, more preferably greater than approximately 10%. For example, steel may contain percentage carbon by weight greater than approximately 0.03%, preferably greater than approximately 0.3%, more preferably greater than approximately 3%. In some embodiments, metal or metal alloys have preferential distribution of corrosion inducing elements on the surface of the implant with surface composition greater than approximately 0.01% by weight of corrosion inducing elements, preferably greater than approximately 5%, more preferably greater than approximately 10% by weight of corrosion inducing elements.

Further, in some embodiments, metals or metal alloys have surface corrosion protective elements less than approximately 15% composition by weight, preferably less than approximately 5%, more preferably less than approximately 1%. For example, an implant alloy such as steel may have a surface composition percentage of chromium being less than approximately 12%, preferably less than approximately 5%, more preferably less than approximately 1%.

Addition of Corrosion Controlling Agents

Alternatively or in addition to the features and elements described above, implants of the present invention may include corrosion controlling agents that control the implant's degradation. The agents may be synthetic or biologic, such as acidic compounds, sodium chloride, calcium chloride, magnesium chloride, hydrochloric acid, citric acid, amino acid, hydroxyapatite, hydrogen peroxide, basic compounds such as potassium hydroxide, acidic and basic pharmaceutical agents, or polymers with acidic or basic byproducts, others or a combination thereof. The amount of agent on the implant can range from approximately 1 nanogram/$cm^2$ to 1000 microgram/$cm^2$, preferably approximately 1 to 500 microgram/$cm^2$, more preferably approximately 10 to 400 microgram/$cm^2$.

In one embodiment, the agent does not significantly induce corrosion of the implant prior to implantation.

In another embodiment, agents are delivered to the tissue adjacent the implant in-situ by several means such as catheter, an infusion balloon, syringe, syringe and needle, or other methods.

Creation of a Corrosion Inducing Galvanic Cell

Figure 18:
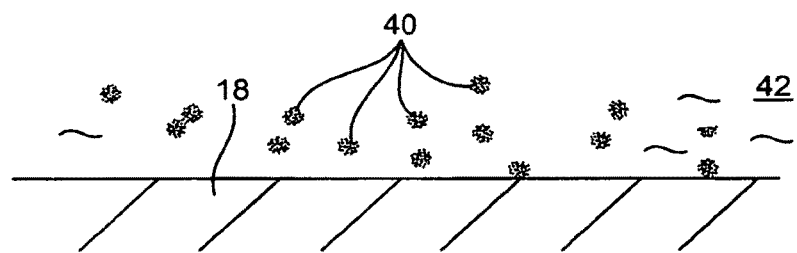
FIG. 18 illustrates an example of particles in fluid or tissue adjacent to an implant.

In some embodiments, metal or alloy particles are delivered adjacent to the implant, either in fluid or tissue. These particles are in fluid contact with the implant and create a corrosion-inducing galvanic cell. Such a galvanic cell controls implant corrosion. FIG. 18 illustrates particles 40 in fluid or tissue 42 adjacent to an implant, such as a stent body 18. The particles are made from metals or alloys that are usually more passive than the implant. In other embodiments non-metallic particles are delivered adjacent to the implant in order to induce corrosion. The particles can range in size from approximately 1 nanometer size to 1 millimeter, preferably ranging from approximately 0.1 micrometer to 10 micrometer so as to minimize tissue response towards them. They can be delivered adjacent to the implant by means such as catheter, an infusion balloon, syringe, syringe and needle, or other methods.

Figure 19:
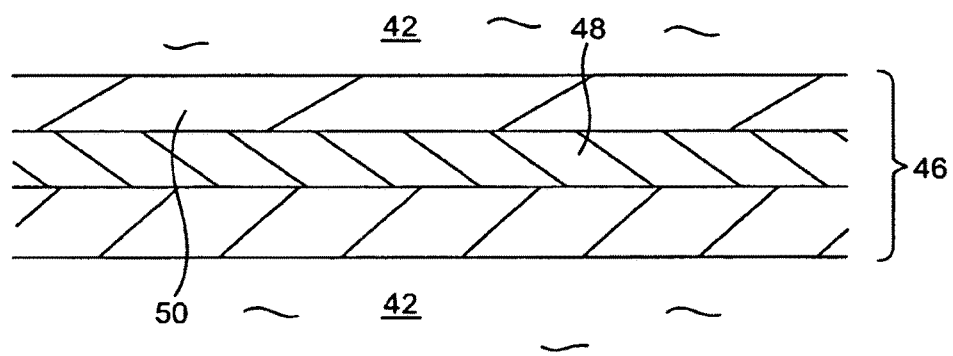
FIG. 19 illustrates an example of a cross-sectional view of an implant having three layers.

FIG. 19 illustrates a cross-sectional view of an implant 46 adjacent to fluid or tissue 42. The implant 46 has three layers wherein the middle layer 48 is comprised of a non-conductive material and the outer layers 50 are comprised of a conductive material, such as metal or alloy, forming a galvanic cell. Any number of layers may be present. Layering will be further described below.

Layering of the Materials

In some embodiments, the implant of the present invention is formed from two or more layers of metal or alloy. In one embodiment, these metals or alloys can be made from different materials which differ in the electrochemical series or/and in different passive state. For example, one layer is made from tungsten while the other is made from chromium. In another example, one layer is made from iron containing alloy while the other is made from silver. In one embodiment, the layers can be in physical contact and in fluid contact upon implantation or after implantation. In one embodiment, the layers are separated by a layer or coating such as polymer, semi-conductor, or a dielectric coating but they are in fluid contact upon implantation or eventually as degradation of the coating occurs. The thickness, surface area, coverage of the layers may vary depending on the desired corrosion rate.

Manipulating Protective Layer

Many metals form an oxide layer on their surface as they corrode. If the oxide layer inhibits further corrosion, the metal is said to passivate. Metals and metal alloys in this state are considered corrosion resistant. Examples of corrosion resistant metal alloys include 316, 316L, 430, 304, 17-7, or other stainless steels, cobalt-chrome alloys (such as L-605, MP35N, Havar, cobalt-20 chromium-15 tungsten-10 nickel alloy, NiTi alloys, or others.

Degradation of these metal alloys can be accelerated or controlled by eliminating or partially eliminating the protective passivation layer in a controlled manner or otherwise preventing the formation of the surface oxide layer. Likewise, the initiation, uniformity, or rate of implant degradation can be controlled by controlling the presence, coverage, thickness, chemical composition, chemical permeability, durability or other aspects of a protective layer such as an oxide layer. For example, the implant can be protected from forming a protective layer such as an oxide layer on its surface by packaging the implant in a low oxygen level environment or depleted oxygen environment. This minimizes oxygen from entering the inside of the package and causing premature corrosion of the implant. In one embodiment, the implant containing product is sealed in a pouch under vacuum. In another embodiment, the pouch is purged with nitrogen, argon or other inert gas. In another embodiment, oxygen scavengers are used to minimize available oxygen content in package. In addition, aspects of the protective layer can be controlled via chemical, mechanical, electrical, thermal means such as via chemical etching, bead blasting, electropolishing, lasing or other means. The protective layer such as oxide layer can be formed, removed, or partially removed in a controlled manner during the manufacturing process or prior to implantation. The layer can also be controlled in situ using a tool or device or other technique such as rotablader, cutting balloon or other technique or other mechanical, electrical, chemical means or combination thereof. Other means to controllably affect the surface composition, characteristics and the degree, thickness, location, or durability of a protective/passive layer can also be used.

Various techniques can be used to alter the passivation layer. In one embodiment, the implant is descaled and electropolished or partially electropolished but not passivated. In another embodiment, the implant is descaled but not electropolished or passivated. In another embodiment, the implant is not descaled or electropolished or passivated.

In one embodiment, the passivation layer thickness is limited to less than 1 nm to provide for controlled degradation, preferably less than 0.5 nm and more preferably less than 0.1 nm. In another embodiment, the layer is only partially covering the surface of the implant to control degradation. This partial coverage can be on one or more surface of the implant or uniformly distributed or non uniformly distributed along the entire length of the implant such as the struts of a stent. For example the amount of corrosion-resistant oxides such as chromium oxides and/or the amount of less corrosion-resistant oxides such as iron oxides in the protective layer can be controlled in order to control degradation. In one embodiment, the protective layer composition is such that the implant degrades in approximately one month to 5 years, preferably 4 months to 2 years, and more preferably 6 months to one year.

In some embodiments, the implant of the present invention can be partially or fully coated with a degradable or non-degradable coating. The coating material can be polymeric, metallic, metallic alloy, ceramic, therapeutic agents, corrosive agents, or radiopaque agents or a combination thereof. The coating can be hydrophobic coating, hydrophilic coating, porous, non-porous, water swellable coating, oxygen barrier, gas permeable barrier, semi-permeable barrier, or other or a combination thereof. The implant can have one or more coatings. In some embodiments, polymer coating can have enhanced porosity by incorporating agents (such as salts, small molecules, blowing agents and the like) into the polymer and leaching the agents out after coating or after implantation. The coating can provide for protection to the tissue wall from the degrading implant, control degradation of the implant, preferentially directing the degradation products, containing degradation products, neutralizing degradation products, releasing agents for therapeutic, corrosion or other purposes, provide radiopacity, or others or combination thereof.

In one embodiment, the coating can be covering at least a portion of the implant surface sections to initiate corrosion of the implant adjacent to or at the uncovered section. For example, a degradable coating preferentially covers the abluminal surface of a vascular stent to preferentially direct the implant degradation products away from the vessel tissue. In another example, the coating preferentially covers the luminal surface of a vascular stent, to control degradation rate of the implant.

In another example the coating has openings on its surface connecting the implant metal or alloy or combination thereof to the electrolyte or fluid to control degradation rate of the implant. In one embodiment, the mean diameter of the opening, width or length can range from approximately 1 nm to 10 mm, preferably approximately 100 nm to 1 mm, more preferably approximately 1 micrometer to 100 micrometer. The length of the opening can further vary based on the length and size of the implant. The size and shape of the openings can be any shape such as circle, square, oval, polygonal, or other uniform or random shapes or combinations thereof. The surface density of openings on the coating of the implant can range from approximately $1/cm^2$ to $1 \times 10^9/cm^2$, preferably approximately $10/cm^2$ to $1 \times 10^6/cm^2$, more preferably approximately $100/cm^2$ to $1 \times 10^3/cm^2$.

In one embodiment, the coating degrades at a slower rate than the implant metal or alloy or combination thereof. This controls the rate of degradation of the implant metal or alloy or combination thereof to achieve longer implant life prior to degradation. In another embodiment, the coating degrades faster than the implant metal or metal alloy or combination thereof. This delays degradation of implant for an initial period. In another embodiment, the coating delays the degradation of the implant for greater than 3 days, preferably greater than one month, more preferably greater than 4 months. In another embodiment, the coating degrades in the body environment ranges from 3 days to 3 years, preferably one month to 2 years, more preferably 4 months to one year. In yet another embodiment, the coating may degrade faster or slower than implant without substantially affecting the degradation rate of the implant. Two or more coating materials may be provided on any one implant device. The coating materials will typically be selected to have different degradation rates and/or different properties in the physiologic environment. Often, two or more coating materials will be layered one over the other so that one layer degrades faster than the other layer(s). Alternatively, the two or more coating materials may be coated over different regions of the exposed surface so that they will often degrade simultaneously, albeit usually at different rates. The different coating materials may also be used to carry different therapeutic and other active agents where it is desired to have different release rates, as described in more detail below.

The thickness of the coating can range from approximately 0.1 nm to 100 micrometer, preferably 1 micrometer to 25 micrometer, more preferably 5 micrometer to 10 micrometer. For some polymeric coatings, the thickness can range from approximately 0.1 micrometer to 100 micrometer, preferably approximately 1 micrometer to 50 micrometer, more preferably approximately 5 micrometer to 25 micrometer. For some metallic or metallic alloy coatings, the thickness can range from approximately 0.1 nm to 100 micrometer, preferably approximately 1 nm to 50 micrometer, more preferably approximately 1 micrometer to 25 micrometer.

Suitable nondegradable or slow degrading coatings include, but are not limited to, polyurethane, polyethylenes imine, cellulose acetate butyrate, ethylene vinyl alcohol copolymer, silicone, C-flex, nylons, polyamide, polyimide, polytetrafluoroethylene (PTFE), parylene, parylast, poly(methyl methacrylate butyrate), poly-N-butyl methacrylate, poly butyl methacrylate copolymer with poly(ethylene vinyl acetate), poly(methyl methacrylate), poly 2-hydroxy ethyl methacrylate, poly ethylene glycol methacrylates, poly vinyl chloride, poly(dimethyl siloxane), poly ethylene vinyl acetate, poly carbonate, poly acrylamide gels, poly maleic anhydride, quarternary ammonium compounds including stearyl ammonium chloride and benzyl ammonium chloride, cellulose acetate butyrate (CAB) and the like, including other synthetic or natural polymeric substances; mixtures, copolymers, or combinations thereof.

Suitable biodegradable coatings include, but are not limited to, poly(lactic acid), poly lactates, poly(glycolic acid), poly glycolates and copolymers and isomers, poly dioxanone, poly(ethyl glutamate), poly(hydroxybutyrate), polyhydroxyvalerate and copolymers, polycaprolactone, polyanhydride, poly(ortho esters); poly(ether esters), poly(iminocarbonates), poly alkylene carbonates such as polyethylene carbonate, poly trimethylene carbonate, starch based polymers, polyester amides, polyester amines, polycyanoacrylates, polyphosphazenes, poly ethylene glycols, poly ethylene oxide, N-vinyl-2-pyrrolidione, copolymers and other aliphatic polyesters, or suitable copolymers thereof including copolymers of poly lactic acids (Poly-D-Lactic acids, Poly-L-Lactic acids, Poly-DL-Lactic acids and the like) and poly-.epsilon.-caprolactone; mixtures, copolymers, or combinations thereof.

Suitable natural coatings include: fibrin, albumin, collagen, gelatin, glycosoaminoglycans, oligosaccharides & poly saccharides, chondroitin, chondroitin sulphates, phosholipids, phosphorylcholine, glycolipids, proteins, cellulose, and mixtures, copolymers, or combinations thereof.

Suitable metallic coatings include tungsten, magnesium, cobalt, zinc, iron, bismuth, tantalum, gold, platinum, stainless steel such as 316L, 304, titanium alloys, semi-metals such as carbon, nanoporous coatings or combination thereof.

The coatings can be applied by following methods which include but are not limited to spraying, dipping, inkjet dispersion, plasma deposition, ion implantation, sputtering, evaporation, vapor deposition, pyrolysis, electroplating, glow discharge coating, or others or combination thereof.

The coating can be comprised of or contain or be adjacent to agents that are synthetic or biologic agents such as salts such as sodium chloride, calcium chloride, magnesium chloride, acidic compounds such as hydrochloric acid, citric acid, amino acid, hydrogen peroxide, basic compounds such as potassium hydroxide, hydroxyapatite, pharmaceutical agents, polymers of acidic or basic byproducts, others or a combination thereof which can control degradation of the implant or coating. The agents contained adjacent to the coatings can range from approximately 1 nanogram/$cm^2$ to 1000 microgram/$cm^2$, preferably approximately 1 to 500 microgram/$cm^2$, more preferably approximately 10 to 400 microgram/$cm^2$.

In one example, the agent covers the surface of the implant with a coating on top. In another example, the agent is mixed with the coating and sprayed on the implant. In another example the coating is the agent.

In one embodiment, the agent does not induce corrosion of the implant prior to implantation. In another embodiment, the agent does not significantly induce corrosion of the implant prior to implantation.

Implants of the present invention may contain degradable or non degradable radio-opaque material or markers or radio-opaque coatings.

Elution of Therapeutic Agents

Implants of the present invention may include pharmacological agents, such as immunomodulators, anti-cancer, anti-proliferative, anti-inflammatory, antithrombotic, anti-platelet, antifungal, antidiabetic, antihyperlipidimia, antiangiogenic, angiogenic, antihypertensive, contraceptives, anti depressants, anti seizures, pain control, anti-addictive, healing promoting drugs, fertility, metabolism control, or other therapeutic classes of drugs or combination thereof. Illustrative immunomodulators agents include but are not limited to rapamycin, everolimus, ABT 578 (Zotarolimus), AP23573 (Ridaforolimus, formerly known as deforolimus), CCI-779 (Temsirolimus), deuterated rapamycin, tacrolimus, cyclosporine, myriocin, their analogues, pro-drugs, salts, or others or combination thereof.

Illustrative anticancer agents include acivicin, aclarubicin, acodazole, acronycine, adozelesin, alanosine, aldesleukin, allopurinol sodium, altretamine, aminoglutethimide, amonafide, ampligen, amusacrine, androgens, anguidine, aphidicolin glycinate, asaley, asparaginase, 5-azacitidine, azathioprine, *Bacillus* calmette-guerin (BCG), beta-2'-deoxythioguanosine, bisantrene hcl, bleomycin sulfate, busulfan, buthionine sulfoximine, BWA 773U82 (Crisnatol mesylate), BW 502U83.HCl (arylmethylaminopropanediols), ceracemide, carbetimer, carboplatin, carmustine, chlorambucil, chloroquinoxaline-sulfonamide, chlorozotocin, chromomycin A3 (Toyomycin), cisplatin, cladribine, corticosteroids, *Corynebacterium parvum*, CPT-11 (Camptothecin-11/Irinotecan), crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution (buffered intrathecal electrolyte/dextrose injection), elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, PALA (N-(phosphonacetyl)-L-aspartic acid), pentostatin, piperazinedione, pipobroman, pirarubicin, piritrexim, piroxantrone hydrochloride, PIXY-321 (granulocyte macrophage colony stimulating factor/interleukin-3 fusion protein), plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864 (1-propanol-3,3'-iminodi-dimethanesulfonate [ester], hydrochloride), zorubicin, epothilone D, epothilone C TAXOL®, such as, paclitaxel, docetaxel, ABJ879 (20-desmethyl-20-methylsulfanyl epothilone B), patupilone, MN-029 (Denibulin), BMS247550 (Ixabepilon), ecteinascidins such as ET-743, tetrahydroisoquinoline alkaloid, sirolimus, actinomycin, methotrexate, antiopeptin, vincristine, mitomycin, 2-chlorodeoxyadenosine or others, antifungal agents such as caspofungin, farnesylated dibenzodiazepinone, ECO-4601 (Dibenzodiazepoine), fluconazole, or others, angiogenesis drugs such as follistatin, leptin, midkine, angiogenin, angiopoietin-1, becaplermin, Regranex, anti-angiogenesis drugs such as canstatin, angiostatin, endostatin, retinoids, tumistatin, vasculostatin, angioarrestin, vasostatin, bevacizumab, prinomastat, or others, antidiabetic drugs such as metformin, hypertension drugs such as candesartan, diovan, diltiazem, atenolol, adalat or others, anti-ischemia drugs such as ranolazine, isosorbide dinitrate, or others.

Illustrative antiinflammatory agents include classic nonsteroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen (Tylenol®), and mixtures thereof; COX-2 inhibitors, such as nimesulide, NS-398 (N-[2-(cyclohexyloxy)-4-nitrophenyl]-methanesulfonamide), flosulid, L-745337 (5-methanesulphonamido-6-(2,4-difluorothiophenyl)-1-indanone), celecoxib, rofecoxib, SC-57666 (1-fluoro-4-(2-(4-(methylsulfonyl)phenyl)cyclopent-1-enyl)benzene), DuP-697 (5-bromo-2-(4-fluorophenyl)-3-(4-methylsulfonylphenyl)thiophene), parecoxib sodium, JTE-522 (4-(4-cyclohexyl-2-methyloxazol-5-yl)-2-fluorobenzenesulfonamide), valdecoxib, SC-58125 (5-(4-Fluorophenyl)-1-[4-(methylsulfonyl)phenyl]-3-(trifluoromethyl)-1H-pyrazole), etoricoxib, RS-57067 (6-[[5-(4-chlorobenzoyl)-1,4-dimethyl-1H-pyrrol-2-yl]methyl]-3 (2H)-pyridazinone), L-748780 (5-Methoxy-2-methyl-1-(2,4,6-trichlorobenzoyl)-1H-indol-3-yl]acetic acid), L-761066 ((R)-4-(1-(4-bromobenzyl)-5-methoxy-2-methyl-1H-indol-3-yl)-3-methylbutanoic acid), APHS (o-(acetoxyphenyl) hept-2-ynyl sulphide), etodolac, meloxicam, S-2474 ((E)-(5)-(3,5-Di-tert-butyl-4-hydroxybenzylidene)-2-ethyl-1,2-isothiazolidine-1,1-dioxide), and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, fluticasone propionate, piroxicam, celeoxib, mefenamic acid, tramadol, meloxicam, methyl prednisone, pseudopterosin, or others, hypercalcemia drugs such as zoledronic acid, alendronate or others, antithrombosis drugs like plavix (clopidogrel), heparin, Arixtra (Fondaparinux Sodium), and Fraxiparine (Nadroparin Calcium) or others or mixtures thereof.

Use of analogues, prodrugs, derivatives, precursors, fragments, salts, or other modifications or variations of pharmaceutical agents are all included.

Analogs, derivatives, prodrugs, salts, synthetic or biologic equivalents of these pharmaceutical agents can be released from the degradable implants depending on the type of treatment needed, such as hyperproliferative diseases, stenosis, wound healing, cancer, aneurysm, diabetic disease, abdominal aortic aneurysm, angiogenesis, hypercalcemia, ischemia, fibrillation, arrhythmia or others.

The agents can be released from the implant using non-degradable, partially degradable, fully degradable coatings or a combination. Illustrative examples of these kinds of coatings have been discussed above. The agents can be incorporated as a matrix with the coating or applied on the implant and covered with the coating as a rate limiting barrier, or the drug directly coated onto the implant surface. In one embodiment, the rate of agent release can be configured to be release at certain times and for certain durations corresponding to the degradation rate of the implant or biological response events within the implant environment. For example, an anti-inflammatory, antiproliferative, or immunomodulator drug or a combination of these can be made to release during the entire degradation period. Multiple drugs can be released to match the degradation rate of the coating and/or degradation rate of the implant. Antiplatelet or anti-thrombotic agents can be released in the initial phase and anti-inflammatory or antiproliferative or immunosuppressants can be released concurrently or at the later phase.

In one embodiment, the agent is, contained or partially contained in the features such as pits, holes, thru holes, streaks, scratches, pores, textures, or others or combination thereof. In another embodiment, the agent is contained in the implant attributes such as reservoirs, trenches, holes, thru holes, channels, between ridges, or other or combination thereof, or combination with one or more of the above. In another embodiment, the agent is applied onto the surface of the implant with a top coat.

The amount of therapeutic or other agent on the implant can range from approximately 1 nanogram/cm$^2$ to 1000 microgram/cm$^2$, preferably approximately 1 to 500 microgram/cm$^2$, more preferably approximately 10 to 400 microgram/cm$^2$. The agent may be released from the implant at rates ranging from approximately 1 nanogram/cm$^2$/day to 1000 microgram/cm$^2$/day, preferably approximately 1 microgram/cm$^2$/day to 200 microgram/cm$^2$/day, more preferably from approximately 5 mcg/cm$^2$/day to 100 mcg/cm$^2$/day. The agent uptake in the tissue adjacent to the implant can range from approximately 0.001 ngm/gm tissue to 1000 microgram/gm tissue, preferably approximately 1 ngm/gm tissue to 100 microgram/gm tissue, more preferably approximately 100 ng/gm tissue to 10 microgram/gm tissue.

In some embodiments, the agent is released from the implant over a period ranging from 1 day to 3 years, preferably 2 weeks to 1 year, more preferably one month to 6 months. In other embodiments, the agent is released from the implant over a period greater than 1 day, preferably greater than 2 weeks, more preferably greater than one month, more preferably greater than 4 months.

It may be appreciated that the agent can be contained within an erodible or non-erodible filament or filaments that are interlaced with the stent or implant.

Degradation of the implant or coating may induce inflammatory response in the body environment. Inflammation can be controlled by pharmacological therapy, provided via systemic or local therapy. Illustrative anti-inflammatory agents include classic non-steroidal anti-inflammatory agents (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen (Tylenol®), and mixtures thereof; COX-2 inhibitors, such as nimesulide, NS-398 (N-[2-(cyclohexyloxy)-4-nitrophenyl]-methanesulfonamide), flosulid, L-745337 (5-methanesulphonamido-6-(2,4-difluorothiophenyl)-1-indanone), celecoxib, rofecoxib, SC-57666 (1-fluoro-4-(2-(4-(methylsulfonyl)phenyl)cyclopent-1-enyl)benzene), DuP-697 (5-bromo-2-(4-fluorophenyl)-3-(4-methylsulfonylphenyl) thiophene), parecoxib sodium, JTE-522 (4-(4-cyclohexyl-2-methyloxazol-5-yl)-2-fluorobenzenesulfonamide), valdecoxib, SC-58125 (5-(4-Fluorophenyl)-1-[4-(methylsulfonyl)phenyl]-3-(trifluoromethyl)-1H-pyrazole), etoricoxib, RS-57067 (6-[[5-(4-chlorobenzoyl)-1,4-dimethyl-1H-pyrrol-2-yl]methyl]-3 (2H)-pyridazinone), L-748780 (5-Methoxy-2-methyl-1-(2,4,6-trichlorobenzoyl)-1H-indol-3-yl]acetic acid), L-761066 ((R)-4-(1-(4-bromobenzyl)-5-methoxy-2-methyl-1H-indol-3-yl)-3-methylbutanoic acid), APHS (o-(acetoxyphenyl)hept-2-ynyl sulphide), etodolac, meloxicam, S-2474 ((E)-(5)-(3,5-Di-tert-butyl-4-hydroxybenzylidene)-2-ethyl-1,2-isothiazolidine-1,1-dioxide), and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, rapamycin or others or analogues of these agents or combination thereof. The anti-inflammatory agents can be coated or incorporated on the implant or preferably given systemically as the implant or coating dissolves in the body environment.

The metal ions from the dissolvable implant may be distributed within the tissue and/or systemically and are excreted from the system eventually which may take a very long time period. Additional therapy like chelation can be used to increase the rate of removal or redistribution of the metallic ions from or within the body. Chelating agents such as ethylenediaminetetraacetate (EDTA) can be given orally or intravenously or local means such as contained by the implant or implant coating or by other means. Sequestering agents can also be used to increase rate of removal or redistribution of metals or metal alloys or combination thereof from or within the body. Illustrative examples of sequestering agents include but are not limited to orthophosphates, orthosilicates, phosphates, others or combination thereof. In one embodiment, the chelating or sequestering agent is delivered to the site with the implant or incorporated within the implant or coating or is applied on the surface of the implant. In another embodiment, the chelating or sequestering agent is control released by a degradable or non degradable coating on the implant. These agents can be selected based on the metallic implant to ensure that the metallic ion is redistributed or eliminated from the system. The agent can also be introduced with an element which can be deposited at the site of the implant as the agent exchanges the element for the metallic ion.

Example 1

A 1.52 mm diameter hole is drilled in the center of a 5 mm diameter cobalt rod by EDM drill or Swiss screw. The rod is then centerless grind to 1.63 mm outer diameter. The resulting cobalt tube is annealed at 850 degrees C. for 1 hr in a vacuum oven. The tube is laser cut into an 18 mm long coronary stent. After the slag and scale are removed by chemical treatment, the stent is placed on a 0.020" diameter metal mandrel and rotated. The air nozzle of a sandblaster (Econoline of Grand Haven, Mich.) with 360 mesh aluminum oxide abrasive blasting media is directed at the stent and air activated for 10 seconds to create a textured surface on all surfaces of the cobalt stent. The stent is cleaned by dipping in hot water beakers several times followed by dipping in 100% isopropanol beaker. The stent is then placed inside a beaker filled with 100% isopropanol. This beaker is placed in an ultrasonic bath (Branson Ultrasonic Corporation of Danbury Conn.) and the stent is cleaned for 5 minutes in the bath. After drying, the stent is crimped onto the balloon of a 3.0×20 mm stent delivery catheter. The stent delivery system is sealed inside a pouch and sterilized by EtO.

The stent delivery system is inserted over a guidewire until the stent is within a lesion in the right coronary artery.

The stent is deployed and the cobalt metal starts to dissolve its mass over a period of time.

Example 2

Before crimping onto a delivery catheter, the coronary stent made in Example 1 is coated with a matrix comprising of 33% Rapamycin and 66% Polyethylene-vinyl alcohol copolymer. After drying, the stent is crimped onto the balloon of a stent delivery catheter. The stent delivery system is sealed inside a pouch and sterilized by EtO.

The stent delivery system is inserted over a guidewire until the stent is within a lesion in the left circumflex artery. The stent is deployed onto the lesion and the cobalt metal starts to dissolve its mass over a period of time while the drug is released.

Example 3

A coronary stent is made from 1.6 mm OD and 0.6 mm ID tungsten rod. The hole is enlarged to 1 mm by an EDM drill. The rod is then centerless grind to 1.11 mm outer diameter. The resulting tungsten tube is annealed at 1400 degrees C. in a vacuum oven for 1 hour. Slots are cut into the tube with a stamp EDM such that a 25 mm long stent pattern is formed. The non EDM ends are removed. After the slag and scale are removed by chemical treatment, the stent is etched for 6 hours in 45 degree Celsius heated 2N Hydrochloric Acid to induce corrosive pit features on its surface.

The stent is cleaned by dipping in hot water beakers several times followed by dipping in 100% ethanol beaker. The stent is then placed inside a beaker filled with 100% ethanol. This beaker is placed in an ultrasonic bath (Branson Ultrasonic Corporation of Danbury Conn.) and the stent is cleaned for 5 minutes in the bath. After drying, the stent is crimped onto the balloon of a 3.5×27 mm stent delivery catheter. The stent delivery system is sealed inside a pouch and sterilized by EtO. After sterilization, the pouch is placed inside a metalized foil pouch. The foil pouch is purged with inert nitrogen gas, evacuated of air, and then sealed.

The stent delivery system is inserted over a guidewire until the stent is within a lesion in the left circumflex artery. The stent is deployed onto the lesion and the tungsten metal starts to dissolve its mass over a period of time.

Example 4

A silver hypotube is cut into a 8 mm coronary stent. After the slag and scale is removed by chemical treatment, the stent is placed in 20 N hydrochloric acid and heated to 200 degrees C. for 1 minute resulting in a corrosive pitted surface features. The stent is cleaned by dipping in boiling water beakers several times followed by dipping in 100% isopropanol beaker. The stent is then placed inside a beaker filled with 100% isopropanol. This beaker is placed in an ultrasonic bath (Branson Ultrasonic Corporation of Danbury Conn.) and the stent is cleaned for 5 minutes in the bath. After drying, the stent is crimped onto the balloon of a 2.5×10 mm stent delivery catheter. A sheath made with oxygen scavenger embedded in the plastic is placed over the crimped stent. The stent delivery system is sealed inside a metalized pouch and sterilized by gamma sterilization.

The stent delivery system is inserted over a guidewire until the stent is within a lesion in the LAD coronary artery. The stent is deployed onto the lesion and the silver metal starts to dissolve its mass over a period of time.

Example 5

An 18 mm coronary stent made in the same way as Example 4 is coated with 200 ug of epothilone D. After drying, the stent is crimped onto the balloon of a 3.25×20 mm stent delivery catheter. The stent delivery system is sealed inside a metalized pouch and sterilized by EtO.

The stent delivery system is inserted over a guidewire until the stent is within a lesion in the right coronary artery. The stent is deployed onto the lesion and the silver metal starts to dissolve its mass over a period of time as the drug is released.

Example 6

A 13 mm urinary tract stent made in the same way as Example 4 is coated with TAXOL® (such as paclitaxel) followed by a coating of polydioxanone. After drying, the stent is crimped onto the balloon of a 3.0×15 mm stent delivery catheter. The stent delivery system is sealed inside a pouch and sterilized by EtO.

The stent delivery system is inserted into and deployed in a blocked section of the urethra. After deployment, the stent metal starts to dissolve its mass into the adjacent tissue and urine over a period of time as the drug is released.

Example 7

A magnesium hypotube is laser cut into a 18 mm coronary stent. After the slag and scale are removed by chemical treatment, the stent is then placed inside a beaker filled with 100% isopropanol. This beaker is placed in an ultrasonic bath (Branson Ultrasonic Corporation of Danbury Conn.) and the stent is cleaned for 5 minutes in the bath. The stent is coated with 1 Angstrom coating of chromium by sputtering. After cleaning and drying, the stent is crimped onto the balloon of a 2.5×20 mm stent delivery catheter. The stent delivery system is sealed inside a pouch and sterilized by EtO.

The stent delivery system is inserted over a guidewire until the stent is at the lesion in the left circumflex coronary artery. The stent is deployed onto the lesion and the magnesium starts to dissolve its mass into the adjacent tissue and blood over a period of time Example 8

A tungsten hypotube is laser cut into a 28 mm long bronchial stent. After the slag and scale is removed by chemical treatment, many small hillocks are deposited on its surface by chemical vapor deposition of tungsten vapors. The hillocks were closely spaced with a Ra of 400 nm. The stent is cleaned by dipping in boiling water beakers several times followed by dipping in 100% isopropanol beaker. After drying, the stent is crimped onto the balloon of a 35×30 mm stent delivery catheter. The stent delivery system is sealed inside a pouch and sterilized by EtO.

The stent delivery system is inserted into a Left mainstem bronchus with cancer. The stent is deployed to keep open the airway block by the tumor while the drug is treating the cancer and the alloy starts to dissolve its mass into the adjacent tissue over a period of time.

Example 9

A 40% bismuth-60% tin tube is secured in a rotating fixture. With the tube turning, the surface of the tube is scratched with a razor blade until the entire outer surface of the tube is scratched. The corrosive scratch features are non-uniformly distributed. The tubing is then laser cut using a femto laser into a 14 mm long aneurysm stent pattern. After the slag and scale is removed by chemical treatment, the stent is cleaned by dipping in boiling water beakers several times followed by dipping in 100% isopropanol beaker. After drying, the stent is crimped onto the balloon of an 2.5×15 mm stent delivery catheter. The stent delivery system is sealed inside a pouch and sterilized by EtO.

The stent delivery system is inserted over a guidewire until the stent is within a brain aneurysm. The stent is deployed onto the aneurysm and the alloy starts to dissolve its mass into the adjacent tissue and blood over a period of time.

Example 10

A rectangular bone plate is made from pure tungsten metal. The plate is immersed in boiling 20N Hydrochloric Acid for 10 minutes to create corrosive pit features and then cleaned with boiling water followed by ultrasonic cleaning in 100% isopropanol. After cleaning, the bone plate is packaged and sterilized with 25 kilogray of gamma radiation. The bone plate is fixed to a fractured femur on either side of the fracture to create a temporary scaffold. The bone plate starts to dissolve its mass into adjacent tissue over a period of time.

Example 11

Figure 20:
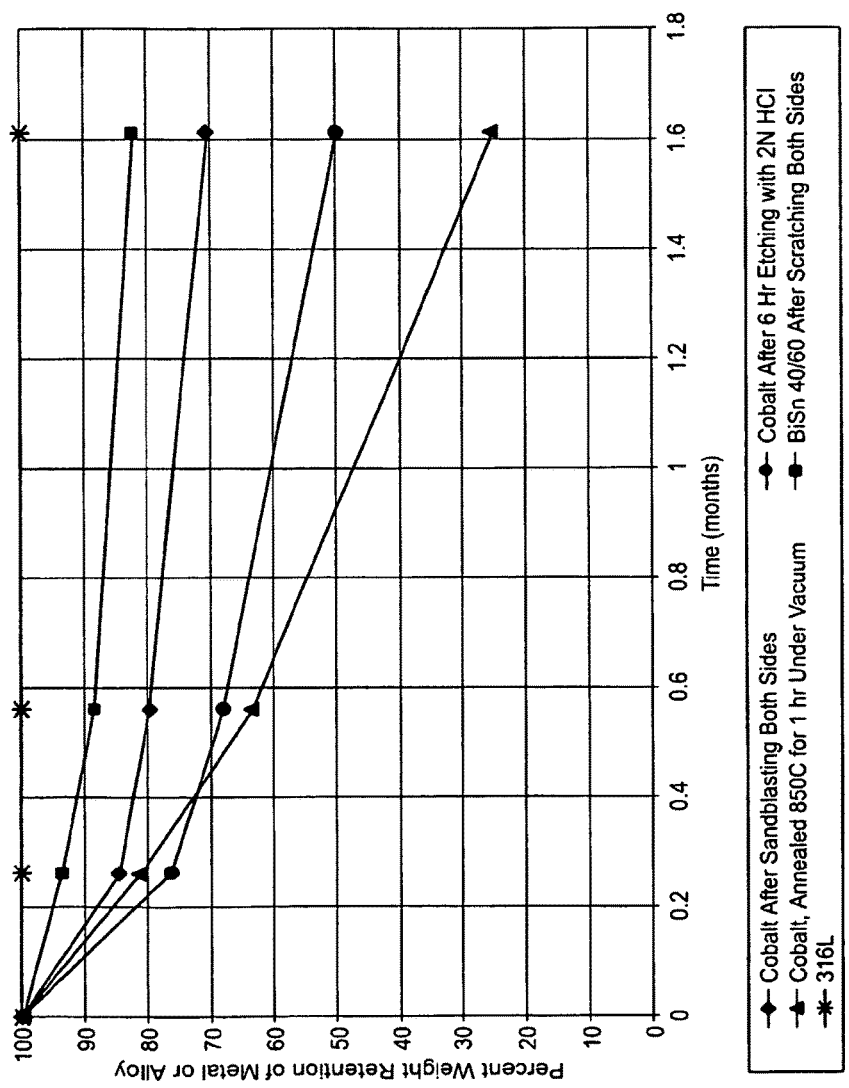
FIGS. 20-21 provide plots showing degradation rates of some metals and alloys with examples of corrosion inducing features.
Figure 21:
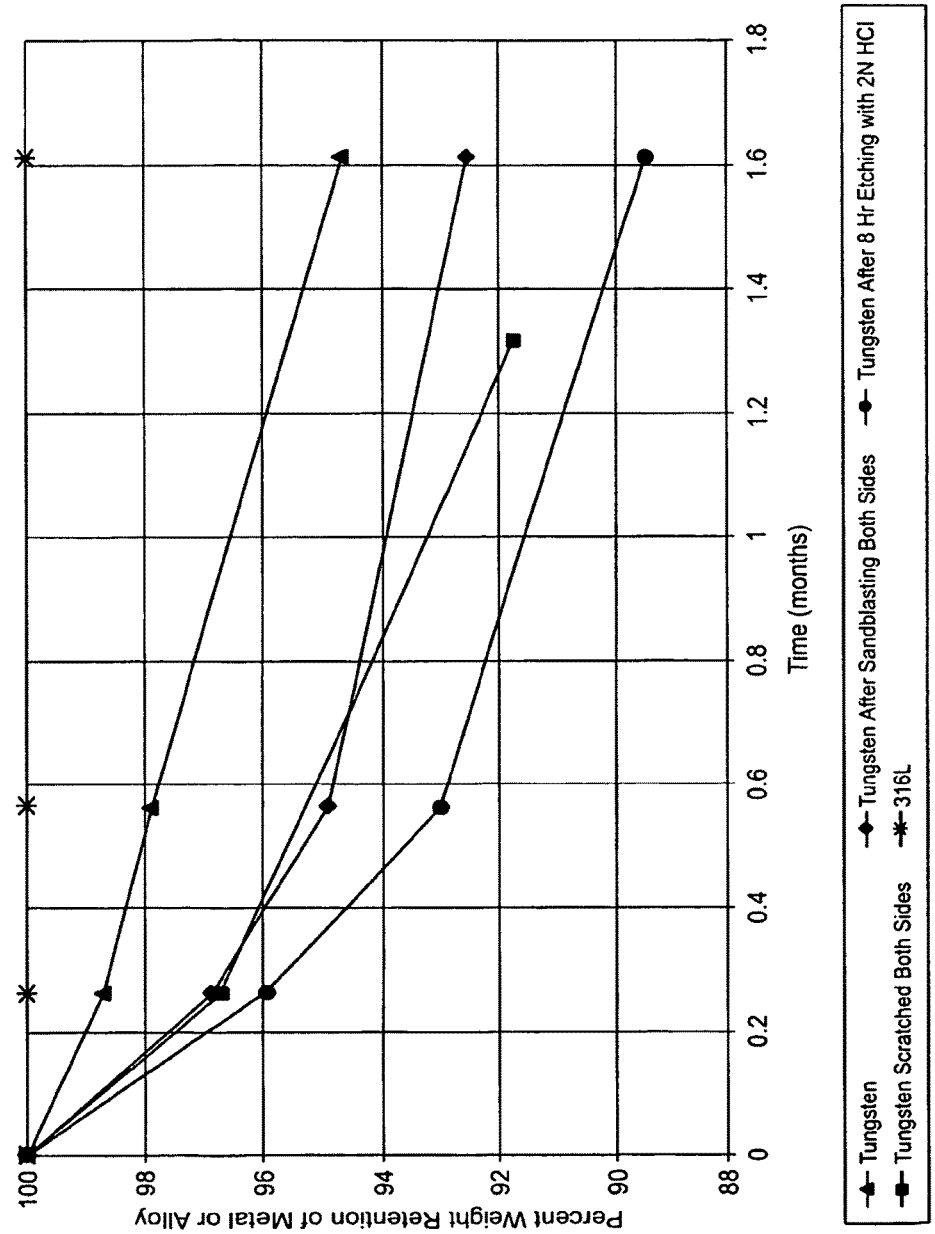

Flat coupons made from cobalt, 40% bismuth-60% indium alloy tungsten, and 316L stainless steel after different treatments were individually weighed. Each coupon was placed inside a vial filled with physiological saline. The vials were heated to 37 degrees C. and rotated at 12 rpm. After time, the coupons were removed from the vials, washed in hot water, and then immersed in a dish filled with 100% isopropanol. The dish was placed in an ultrasonic bath for 5 minutes. Plots showing the amount of rate loss from the metals and alloy are shown in FIGS. 20-21.

Example 12

A 1010 carbon steel tube is laser cut into a 14 mm long coronary stent. The stent is annealed for 90 minutes at 750 C in a furnace. The stent is then cleaned and secured in a rotating fixture. The stent is sandblasted with 20 micron aluminum oxide media until the slag and scale is removed and surface of the stent is textured with 400 nm Ra roughness. After cleaning, the stent is coated with 10 micron polyethylene carbonate containing 30% rapamycin analogue and crimped onto the balloon of an 3.5×15 mm stent delivery catheter. The stent delivery system is sealed inside a pouch and sterilized by Ebeam.

The stent delivery system is inserted over a guidewire until the stent is within a coronary artery. The stent is deployed onto the coronary artery and the alloy starts to dissolve its mass into the adjacent tissue and blood over a period of time.

Example 13

A cobalt foil is laser cut into a 25 mm flat patterned coronary stent. The foil is annealed for 90 minutes at 700 C in a vacuum furnace. The stent is then descaled with HCl and cleaned. After cleaning, one side (luminal side) of the patterned foil is coated with 1 micron thick PLLA. The stent is then welded into a tubular stent. After cleaning, the stent is fully coated with 5 micron thick polyethylene carbonate containing 40% rapamycin analogue and crimped onto the balloon of an 3.0×26 mm stent delivery catheter. The stent delivery system is sealed inside a pouch. The pouch is placed inside a cooled container and the container is exposed to Ebeam to sterilize the stent system.

The stent delivery system is inserted over a guidewire until the stent is within a coronary artery. The stent is deployed onto the coronary artery and the alloy starts to dissolve its mass into the adjacent tissue and blood over a period of time.

Example 14

A 1010 carbon steel tube is laser cut into a 14 mm long coronary stent. The stent is annealed for 90 minutes at 750 C in a furnace. The stent is then cleaned and secured in a rotating fixture. The stent is sandblasted with 20 micron aluminum oxide media until the slag and scale is removed and surface of the stent is textured to a roughness (Ra) of 400 nm. After cleaning, the stent is coated with 150 microgram of rapamycin analogue and crimped onto the balloon of an 3.5×15 mm stent delivery catheter. The stent delivery system is sealed inside a pouch and sterilized by Ebeam.

The stent delivery system is inserted over a guidewire until the stent is within a coronary artery. The stent is deployed onto the coronary artery and the alloy starts to dissolve its mass into the adjacent tissue and blood over a period of time.

The various embodiments, examples, and components within this application can apply separately or in combination with one another throughout this application.

All publications and patent applications cited in this specification are herein incorporated by reference as if each individual publication or patent application were specifically and individually indicated to be incorporated by reference.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A degradable, implantable stent comprising:
    a tubular body comprising a corrodible metal or metal alloy including at least one corrosion enhancing element within the corrodible metal or metal alloy and at least one corrosion resisting element; and
    a passivation layer or a coating incorporated in or covering at least a portion of the body;
    wherein one metal in the corrodible metal alloy comprises at least 90% of the metal alloy; and
    wherein said stent degrades in about one month to about five years in a physiological environment.

2. A stent of claim 1, wherein the metal alloy is selected from the group consisting of bismuth, cobalt, copper, indium, iridium, iron, magnesium, molybdenum, nickel, niobium, silver, tin, tungsten, zinc, zirconium and combinations thereof.

3. A stent of claim 1 wherein the metal comprises bismuth, carbon, chromium, cobalt, copper, indium, iridium, iron, magnesium, molybdenum, nickel, niobium, silicon, silver, tin, titanium, tungsten, vanadium, zinc, zirconium, or a combination thereof.

4. A stent of claim 1, wherein the corrosion enhancing agent is selected from the group consisting of calcium, carbon, copper, iron, magnesium, sulfide, silicon, silicates, sulfur, and combinations thereof.

5. A stent of claim 1, wherein the corrosion resisting element comprises chromium, nickel or molybdenum.

6. A stent of claim 1, wherein the at least one corrosion enhancing element is greater than approximately 0.01% of the corrodible metal or metal alloy composition by weight.

7. A stent of claim 1, wherein the at least one corrosion resisting element is less than approximately 15% of the corrodible metal or metal alloy composition by weight.

8. A stent as in claim 1, wherein the coating covers at least a portion of the tubular body and the coating comprises a degradable polymer.

9. A stent as in claim 8, wherein the degradable polymer is selected from the group consisting of poly(lactic acids), poly(D-lactic acid), poly(L-lactic acid), poly(DL-lactic acid), copolymers of poly(lactic acids), poly lactates, poly(glycolic acid), poly glycolates, poly dioxanone, poly(ethyl glutamate), poly(hydroxybutyrate), polyhydroxyvalerate, poly (ε-caprolactone), polyanhydride, poly(ortho esters); poly(ether esters), poly (iminocarbonates), poly alkylene carbonates, polyethylene carbonate, poly trimethylene carbonate, starch based polymers, polyester amides, polyester amines, polycyanoacrylates, polyphosphazenes, poly ethylene glycols, poly ethylene oxide, N-vinyl-2-pyrrolidone, aliphatic polyesters, copolymers of poly(D-lactic acid) and poly(ε-caprolactone), copolymers of poly(L-lactic acid) and poly(ε-caprolactone), and copolymers of poly(DL-lactic acid) and poly(ε-caprolactone).

10. A stent as in claim 1, further comprising at least one therapeutic agent.

11. A stent as in claim 10, wherein at least one of the therapeutic agents is selected from the group consisting of immunomodulators, anti-cancer agents, anti-proliferative agents, anti-inflammatory agents, antithrombotic agents, antiplatelet agents, antifungal agents, antidiabetic agents, antihyperlipidimia agents, antiangiogenic agents, angiogenic agents, antihypertensive agents, contraceptive agents, anti depressant agents, anti seizure agents, pain control agents, anti-addictive agents, healing promoting drugs, fertility agents, metabolism control agents, and combinations thereof.

12. A stent as in claim 10, wherein at least one of the therapeutic agents is selected from the group consisting of acivicin, aclarubicin, acodazole, acronycine, adozelesin, alanosine, aldesleukin, allopurinol sodium, altretamine, aminoglutethimide, amonafide, ampligen, amusacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene HCl, bleomycin sulfate, busulfan, buthionine sulfoximine, BWA 773U82 (Crisnatol mesylate), BW 502U83.HCl (arylmethylaminopropanediols), ceracemide, carbetimer, carboplatin, carmustine, chlorambucil, chloroquinoxaline-sulfonamide, chlorozotocin, chromomycin A3 (Toyomycin), cisplatin, cladribine, corticosteroids, *Corynebacterium parvum*, CPT-11 (Camptothecin-11/Irinotecan), crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, buffered intrathecal electrolyte/dextrose injection, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, 20% intravascular perflurochemical emulsion, flutamide, gallium nitrate, gemcitabine, goserelin acetate, hepsulfam, hexamethylene bisacetamide, homoharringtonine, hydrazine sulfate, 4-hydroxyandrostenedione, hydroxyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, PALA (N-(phosphonacetyl)-L-aspartic acid), pentostatin, piperazinedione, pipobroman, pirarubicin, piritrexim, piroxantrone hydrochloride, granulocyte macrophage colony stimulating factor/interleukin-3 fusion protein (PIXY-321), plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864 (1-propanol-3,3'-iminodi-dimethanesulfonate [ester], hydrochloride), zorubicin, epothilone D, epothilone C, paclitaxel, docetaxel, ABJ879 (20-desmethyl-20-methylsulfanyl epothilone B), patupilone, MN-029 (Denibulin), BMS247550 (Ixabepilon), ecteinascidins, tetrahydroisoquinoline alkaloid, sirolimus, actinomycin, methotrexate, antiopeptin, vincristine, mitomycin, 2-chlorodeoxyadenosine, caspofungin, farnesylated dibenzodiazepinone, ECO-4601 (Dibenzodiazepoine), fluconazole, follistatin, leptin, midkine, angiogenin, angiopoietin-1, becaplermin, canstatin, angiostatin, endostatin, retinoids, tumistatin, vasculostatin, angioarrestin, vasostatin, bevacizumab, prinomastat, metformin, candesartan, diovan, diltiazem, atenolol, adalat, ranolazine, isosorbide dinitrate, rapamycin, everolimus, ABT 578 (Zotarolimus), AP23573 (Ridaforolimus, formerly known as deforolimus), CCI-779 (Temsirolimus), deuterated rapamycin, tacrolimus, cyclosporine, myriocin, aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nabumetone, acetaminophen, COX-2 inhibitors, nimesulide, NS-398 (N-[2-(cyclohexyloxy)-4-nitrophenyl]-methanesulfonamide), flosulid, L-745337 (5-methanesulphonamido-6-(2,4-difluorothiophenyl)-1-indanone), celecoxib, rofecoxib, SC-57666 (1-fluoro-4-(2-(4-(methylsulfonyl)phenyl)cyclopent-1-enyl)benzene), DuP-697 (5-bromo-2-(4-fluorophenyl)-3-(4-methylsulfonylphenyl)thiophene), parecoxib sodium, JTE-522 (4-(4-cyclohexyl-2-methyloxazol-5-yl)-2-fluorobenzenesulfonamide), valdecoxib, SC-58125 (5-(4-Fluorophenyl)-1-[4-(methylsulfonyl)phenyl]-3-(trifluoromethyl)-1H-pyrazole), etoricoxib, RS-57067 (6-[[5-(4-chlorobenzoyl)-1,4-dimethyl-1H-pyrrol-2-yl]methyl]-3 (2H)-pyridazinone), L-48780 (5-Methoxy-2-methyl-1-(2,4, 6-trichlorobenzoyl)-1H-indol-3-yl]acetic acid), L-761066

((R)-4-(1-(4-bromobenzyl)-5-methoxy-2-methyl-1H-indol-3-yl)-3-methylbutanoic acid), APHS (o-(acetoxyphenyl) hept-2-ynyl sulphide), etodolac, meloxicam, S-2474 ((E)-(5)-(3,5-Di-tert-butyl-4-hydroxybenzylidene)-2-ethyl-1,2-isothiazolidine-1,1-dioxide), glucocorticoids, hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, fluticasone propionate, piroxicam, celeoxib, mefenamic acid, tramadol, meloxicam, methyl prednisone, pseudopterosin, hypercalcemia drugs, zoledronic acid, alendronate, antithrombosis drugs, heparin, clopidogrel, Fondaparinux Sodium, Nadroparin Calcium, and analogues, prodrugs, derivatives, precursors, fragments, salts, modifications and variations thereof.

13. A stent as in claim 1, wherein the passivation layer or the coating comprises a metal, a metal alloy, an oxide of a metal, an oxide of a metal alloy, a ceramic, a radiopaque agent, a polymer, or a combination thereof.

14. A stent as in claim 13, wherein the polymer is selected from the group consisting of polyurethane, polyethylenes imine, ethylene vinyl alcohol copolymer, silicone, thermoplastic elastomer, nylons, polyamide, polyimide, polytetrafluoroethylene (PTFE), parylene, parylast, poly(methyl methacrylate butyrate), poly-n-butyl methacrylate, poly butyl methacrylate copolymer with poly(ethylene vinyl acetate), poly(methyl methacrylate), poly 2-hydroxy ethyl methacrylate, poly ethylene glycol methacrylates, poly vinyl chloride, poly(dimethyl siloxane), poly ethylene vinyl acetate, poly carbonate, poly acrylamide gels, poly maleic anhydride, cellulose, cellulose acetate butyrate, proteins, fibrin, albumin, collagen, gelatin, oligosaccharides, polysaccharides, glycosoaminoglycans, chondroitin, chondroitin sulphates, phosholipids, phosphorylcholine, glycolipids; mixtures, copolymers, and combinations thereof.

15. A stent as in claim 1, wherein the passivation layer or the coating degrades at a slower rate than the body.

16. A stent as in claim 1, wherein the passivation layer or the coating slows down or delays degradation of the body.

17. A stent as in claim 1, wherein the passivation layer or the coating is non-porous or porous.

18. A stent as in claim 1, wherein the stent maintains greater than about 25% of strength after one month from implantation.

19. A stent as in claim 1, wherein the stent maintains greater than about 50% of strength after two months from implantation.

20. A stent as in claim 1, wherein the stent maintains greater than about 25% of strength after four months from implantation.

21. A stent as in claim 1, wherein the passivation layer thickness is less than 1 nm.

22. A stent as in claim 1, wherein the coating thickness ranges from 0.1 nm to 100 micrometer.

23. A stent as in claim 1, wherein the stent degrades in about four months to about two years in a physiological environment.

24. A stent as in claim 1, wherein the stent degrades in about six months to about one year in a physiological environment.

25. A stent as in claim 1, wherein the passivation layer or the coating comprises a degradation controlling element.

26. A stent as in claim 1, wherein the coating comprises a therapeutic agent.

27. A stent as in claim 26, wherein the therapeutic agent is in a polymer coating.

28. A stent as in claim 1, wherein the coating comprises a polymer.

29. A stent as in claim 28, wherein the polymer is fully degradable.

30. A stent as in claim 1, wherein the metal alloy is a zinc alloy.

31. A stent as in claim 1, wherein the corrosion resisting element is not corrodible.

32. A stent as in claim 1, wherein the stent further comprises a corrosion-inducing surface feature which causes at least a portion of the tubular body to degrade at a controlled degradation rate.

33. A stent as in claim 1, wherein at least one of said elements is not a metal.

34. A stent as in claim 1, wherein the degradation of the stent produces degradation byproducts which are physiologically benign.

35. A stent as in claim 1, wherein the stent further comprises at least one radiopaque marker.

36. A stent as in claim 1, wherein the stent further comprises degradable or non-degradable radiopaque markers or radiopaque coating.

37. A stent as in claim 1, wherein the degradation of the stent produces by products which are naturally occurring in a physiological environment.

38. A stent as in claim 1, wherein the stent has a variable degradation rate along its structure.

39. A stent as in claim 1, wherein the stent has at least two different degradation rates.

40. A stent as in claim 1, wherein the ends of the stent degrade faster than the area in between the ends.

41. A stent as in claim 1, wherein said coating degrades at a slower rate than the corrodible metal alloy.

42. A stent as in claim 1, wherein degradation of the stent or coating induces an inflammatory response in a body environment.

43. A stent as in claim 42, wherein said stent further comprises a therapeutic agent to treat inflammation.

44. A stent as in claim 1, wherein said body is formed from a metal hypotube.

45. A stent as in claim 1, wherein the stent has an average mass percentage loss of approximately 3% per day to 0.05% per day.

46. A stent as in claim 1, wherein the stent has an Icorr of 0.0001 amps/cm$^2$ to 0.1 amps/cm$^2$.

47. A stent as in claim 1 wherein the stent has an abluminal and luminal surfaces and the coating covers the abluminal surface of the stent.

48. A stent as in claim 1 wherein the stent has an abluminal and luminal surfaces and the coating covers the luminal surface of the stent.

* * * * *